(12) United States Patent
Reznik et al.

(10) Patent No.: US 8,263,571 B2
(45) Date of Patent: Sep. 11, 2012

(54) GENE SILENCING OF THE BROTHER OF THE REGULATOR OF IMPRINTED SITES (BORIS)

(75) Inventors: Boris N. Reznik, Aventura, FL (US); Christopher J. Dougherty, Lake Worth, FL (US); Thomas Ichim, San Diego, CA (US)

(73) Assignee: Vendevia Group, LLC, Hollywood, FL (US)

( * ) Notice: Subject to any disclaimer, the term of this patent is extended or adjusted under 35 U.S.C. 154(b) by 132 days.

(21) Appl. No.: 12/673,003

(22) PCT Filed: Aug. 11, 2008

(86) PCT No.: PCT/US2008/072829
§ 371 (c)(1),
(2), (4) Date: Jul. 14, 2010

(87) PCT Pub. No.: WO2009/035804
PCT Pub. Date: Mar. 19, 2009

(65) Prior Publication Data
US 2010/0279291 A1 Nov. 4, 2010

Related U.S. Application Data

(60) Provisional application No. 60/955,263, filed on Aug. 10, 2007.

(51) Int. Cl.
*A61K 31/70* (2006.01)
*C07H 21/04* (2006.01)
(52) U.S. Cl. ......................................... 514/44; 536/24.5
(58) Field of Classification Search ........................ None
See application file for complete search history.

(56) References Cited

U.S. PATENT DOCUMENTS
7,691,997 B2 * 4/2010 Khvorova et al. ........... 536/24.5

FOREIGN PATENT DOCUMENTS
WO    WO 2008028066 A2 * 3/2008

OTHER PUBLICATIONS
Vatolin et al. Cancer Research 2005, vol. 65, pp. 7751-7762.*

* cited by examiner

*Primary Examiner* — Tracy Vivlemore
(74) *Attorney, Agent, or Firm* — The Law Office of Jane K. Babin, Professional Corporation; Jane K. Babin

(57) ABSTRACT

The present invention provides methods and compositions useful for inhibiting expression of the gene encoding the transcription factor, Brother of the Regulatory of Imprinted Sites (BORIS) by RNA interference. Methods of the present invention can be used to silence BORIS in cancer cells, which results in apoptosis and may be useful as for treating cancer in mammals. The methods of the invention directed to cancer therapy can be used alone or in combination with standard cancer treatments such as surgery, radiation, chemotherapy, and immunotherapy.

19 Claims, 7 Drawing Sheets

GENE SILENCING OF THE BROTHER OF THE REGULATOR OF IMPRINTED SITES (BORIS)

RELATED APPLICATIONS

The present application claims the benefit of priority to U.S. Provisional Application No. 60/955,263 filed Aug. 10, 2007, and to PCT International Application Number PCT/US08/72829 filed Aug. 11, 2008 the entire contents of which are incorporated herein by reference.

FIELD OF THE INVENTION

The present invention relates generally to the field of cancer therapeutics, and particularly to the use of RNA interference to silence an oncogene. More specifically, the invention relates to the use of small interfering RNA (siRNA) to inhibit expression of the Brother of the Regulator of Imprinted Sites (BORIS).

BACKGROUND

RNA Interference

RNA interference (RNAi) is a process by which a double-stranded RNA (dsRNA) selectively inactivates homologous mRNA transcripts by triggering specific degradation of homologous RNAs in the cell. RNAi is more potent than anti-sense technology, giving effective knockdown of gene expression with as little as 1-3 molecules of duplex RNA per cell. Furthermore, inhibition of gene expression can migrate from cell to cell and may even be passed from one generation of cells to another.

Traditionally, RNAi has required long pieces (200-800 base pairs) of dsRNA to be effective. This is impractical for therapeutic uses due to the sensitivity of long RNA molecules to cleavage by RNases found in the plasma and intracellularly. In addition, long pieces of dsRNA have been reported to induce panic responses in eukaryotic cells, which include nonspecific inhibition of gene transcription, but also production of interferon-α.

When long dsRNA duplexes enter the cytoplasm, an RNase III type enzymatic activity cleaves the duplex into smaller, 21-23 base-pairs molecules, termed small interfering RNA (siRNA). Short RNA duplexes are active in silencing gene expression but do not trigger nonspecific panic responses when less than 30 nucleotides in length. Moreover, siRNAs can be administered directly to a cell or organism to silence gene expression, thereby obviating the need to use long dsRNA or less effective single-strand anti-sense RNA, ribozymes, or the like.

siRNA has been found effective for inhibiting expression of a variety of genes in mammalian cells in vitro and in vivo. siRNA technology provides an appealing approach for selectively inhibiting gene expression in clinical and therapeutic settings due to many advantages over conventional gene and antibody blocking approaches, including: (1) potent inhibitory efficacy; (2) specificity—even a single nucleotide mismatch can be distinguished; (3) inhibitory effects that can be passed to daughter cells for multiple generations; (4) high in vitro transfection efficiency; (5) practicality for in vivo use due to short sequence length, low effective concentrations and lack of neutralizing antibody production; (6) availability of tissue- and cell-specific targeting (e.g. via inducible or promoter-specific vectors, ligand-directed liposomes or antibody-conjugated liposomes); and (7) possibility of simultaneously silencing multiple genes or multiple exons in a single gene.

Nevertheless, siRNA approaches are not without limitations. Not all 21-23 nucleotide regions in a gene can be effectively targeted. Certain positions within the siRNA appear to be more important than others for effectively inhibiting gene expression. Furthermore, "off-target" effects (i.e., silencing expression of unintended genes) can be seen with as short as a 6-7 nucleotide match between the siRNA and an off-target gene, in some cases leading to non-specific, toxic effects. Although progress is being made toward understanding the importance of these factors and devising formulas and algorithms for siRNA design, the selection of effective siRNAs remains at least in part an empirical exercise.

The Brother of the Regulator of Imprinted Sites (BORIS)

The BORIS gene encodes a germ line, testis- and cancer-specific, paralog of the CTCF (CCCTC-binding factor; GenBank Accession No.: NM_006565), and is an epigenetically-acting transcription factor that represses the tumor inhibitor functions of CTCF. Thus, BORIS is also referred to as CTCFL for CTCF-like. BORIS contains a central DNA-binding domain that is nearly identical to CTCF, but differs in N and C termini amino acid sequence, thereby suggesting that BORIS could play a role of interfering with CTCF-driven regulatory pathways if it is abnormally expressed in somatic cells (Klenova et al., Semin. Cancer Biol. (2002) 12:399-414; Loukinov et al., Proc. Natl. Acad. Sci. USA (2002) 99:6806-11).

Abnormal activation of BORIS has been observed in all human primary tumors and cancer cell lines tested, including breast, lung, skin, bone, brain, colon, prostate, pancreas, mast cell, ovarian and uterine cancers, with increased expression associated with advanced stage of disease (see e.g., Ulaner et al., Hum. Mol. Genet. (2003)12:535-49; Vatolin et al., Cancer Res (2005) 65:7751-62; Hong et al., Cancer Res (2005) 65:7763-74; and Loukinov et al, J. Cell. Biochem. (2006) 98:1037-43; D'Arcy et al, Br. J. Cancer (2008) 98:571-9). BORIS induces de-repression of many genes associated with malignancy (Vatolin et al., Cancer Res (2005) 65:7751-62; Hong et al., Cancer Res (2005) 65:7763-74), and ectopic expression of BORIS in normal cells has been reported to result in classic features of cell-transformation (see Ghochikyan et al., J. Immunol. (2007) 178: 566-73).

BORIS reportedly competes with CTCF for shared DNA target sites and can tether epigenetic modifications to and around such sites, resulting in modulation of gene expression (see Vatolin et al., Cancer Res (2005) 65:7751-62; Hong et al., Cancer Res (2005) 65:7763-74; Ghochikyan et al., J. Immunol. (2007) 178: 566-73). BORIS can also bind methylated DNA target sites, while there is evidence that CTCF cannot (see Nguyen et al., Cancer Res (2008) 68:5546-51). Therefore, BORIS can be classified as a unique cancer-testis gene with cell-transforming activity that is most likely mediated by competition with somatic tumor suppressor CTCF through epigenetic modifications (Vatolin et al., Cancer Res (2005) 65:7751-62).

Previous studies have demonstrated the potential of BORIS as a target for anti-cancer therapeutics. Protein-based, but not DNA-based, BORIS vaccine induced a significant level of antibody production in immunized animals, leading to breast cancer regression. Interestingly, potent anticancer $CD8^-$-cytotoxic lymphocytes were generated after immunization with a DNA-based, but not protein-based, BORIS vaccine. (Ghochikyan et al., J. Immunol. (2007) 178: 566-73). However, the applicability of immunological approaches to cancer treatment is subject to limitations, including a) tumor suppression of the host immune system through active production of soluble and membrane bound factors; b) ability of tumor cells to lose expression of antigen processing machinery; and c) possibility of a deficit in the immunological repertoire of cancer patients caused by down regulation of TCR zeta chain expression.

BORIS is a particularly appealing target for cancer therapy for several reasons. First, the widespread distribution of BORIS in different types of cancer cells coupled with the general concept that while non-malignant cells do not require activated oncogenes for survival, the suppression of an activated oncogene in a cancer cell often leads to apoptosis, suggests that therapies targeting BORIS may be effective for selective killing of a large number of cancer cell types. Thus, a single approach to cancer therapy may be applicable to many forms of cancer. Furthermore, BORIS is limited to testes and cancer cell types, and is not found in the vast majority of normal cell types. Therapies directed at BORIS are expected to have fewer side effects than others that target molecules or mechanisms present in normal cells, particularly in women where BORIS is not found in normal tissues.

Thus, there is an interest in developing anti-BORIS therapies for cancer, particularly in malignancies of the female reproductive system such as breast and ovarian cancer.

SUMMARY OF THE INVENTION

The present invention provides method of inhibiting expression of Brother of the Regulator of Imprinted Sites (BORIS) in a cell by introducing into the cell a small interfering RNA (siRNA) molecule that directs cleavage of BORIS mRNA, thereby inhibiting expression of BORIS in the cell. The small interfering RNA (siRNA) molecule does not inhibit expression of paralogous CTCF mRNA sequences in the cell.

The siRNA can be chemically or enzymatically synthesized. In certain embodiments of the invention, the siRNA molecule is synthesized from a polynucleotide template (e.g. a construct) that encodes the siRNA molecule or a precursor of the siRNA. In certain aspects, the siRNA is synthesized from the polynucleotide in the cell.

The siRNA molecule can be a double-strand RNA, RNA-DNA chimera or RNA-DNA hybrid and may contain modifications of sugars, bases or phosphodiester linkages in the polynucleotide. Typical siRNAs of the invention are about 19-24 base pairs in length, and more often about 21-22 base pairs in length.

In certain embodiments of the invention, the siRNA is a duplex consisting of a sense strand and an antisense strand, where each strand is 19-24 nucleotides in length; the duplex has 19-24 base pairs; the antisense strand is complementary to a target RNA encoded by the BORIS gene; and the sense strand and the antisense strand are complementary to each other. Typically, one strand of such siRNA is at least about 90%, 95% or 99% identical to a 19-24 nucleotide sequence of the BORIS gene. In one aspect, one strand of the siRNA has a nucleotide sequence selected from SEQ ID NOs:1-61, such as a nucleotide sequence of SEQ ID NOs:59 or SEQ ID NO: 60. In another aspect, one strand of the siRNA has a nucleotide sequence selected from SEQ ID NOs:62-123.

Inhibiting expression of BORIS in the cell can induce apoptosis by activating one or more DEVD-recognizing caspase in the cell.

The cells are typically mammalian, such as human. In some embodiments the cell is a cancer cell, which may be present in a human patient, such as in a tumor. The cancer cell can be a breast, lung, skin, bone, brain, colon, prostate, pancreas, mast cell, ovarian or uterine cancer cell in which BORIS functions as an oncogene.

Also provided by the invention are siRNA molecules that direct cleavage of BORIS mRNA. Exemplary siRNAs contain one strand that has a nucleotide sequence selected from SEQ ID NOs:1-123, which may be SEQ ID NO:59 (OCM-8054) or SEQ ID NO:60 (OCM-8055). For example the siRNA can be SEQ ID NO:59 and its full complement, or SEQ ID NO:60 and its full complement. In certain embodiments the siRNA has at least one 3' overhang that is 1-3 nucleotides in length. For example, the siRNA can be a duplex formed by SEQ ID NOs:59 and 62 or a duplex formed by SEQ ID NOs:60 and 63.

The present invention further provides methods for treating cancer in a subject by introducing into a cancer cell an siRNA molecule that directs cleavage of BORIS mRNA. The subject can be a human female, and the cancer can be, for example breast cancer or glioblastoma. According to certain methods of the invention, siRNA can be introduced into the cell by transfection, e.g. using a chemical transfection agent, such as a phospholipid, a cationic lipid, a cationic polymer, a natural polymer; chitosan, atelocollagen, a synthetic polymer, poly (L-lysine), PEI, a dendrimer, a poly(ethylene glycol), DOTAP, AtuFECT01/DphPE, LIC-101; 2-O-(2-diethyl-aminoethyl)-carbamoyl-1, 3-O-dioleoylglycerol, phosphatidylcholine, DlinDMA, DSPC, or cholesterol. For delivery into the cell, the siRNA can be encapsulated in a nanoparticle, a liposome or a microbubble, which can be coated with an agent having affinity for the cancer cell.

To improve transfection, the cancer cell can be exposed to ultrasound at a frequency sufficient to allow transfection to occur. Alternatively, the siRNA can be introduced in into the cell by electroporation or hydrodynamic methods.

The siRNA can be locally administered (e.g., by intratumor injection or topical application) or it can be systemically administered (e.g. by intravenous injection or oral administration).

In certain embodiments, introducing the siRNA into the cell includes transfecting a polynucleotide that encodes the siRNA or a precursor of the siRNA into the cell, which leads to synthesis of the siRNA in the cell from the polynucleotide. In certain embodiments, the polynucleotide may be included in a viral genome and/or encapsulated in viral particle which is then introduced into the cell by infection.

According to the methods of the invention for treating cancer, siRNA can be administered together with a chemotherapeutic agent, an immunotherapeutic agent, or both a chemotherapeutic agent and an immunotherapeutic agent. The immunotherapeutic can be, for example, an innate immune stimulator, or a stimulator of adaptive immunity.

The invention also provides methods for inhibiting expression of BORIS variants in a cell by first detecting expression of a BORIS variant in the cell (e.g., by PCR of RNA, or immunological detection of BORIS epitopes) and then introducing into the cell a small interfering siRNA molecule that directs cleavage of an mRNA encoding the variant BORIS, thereby inhibiting expression of the variant BORIS in the cell. According to this embodiment, the variant can, for example, be a splice variant, truncation or deletion variant.

DETAILED DESCRIPTION

Figure 1:
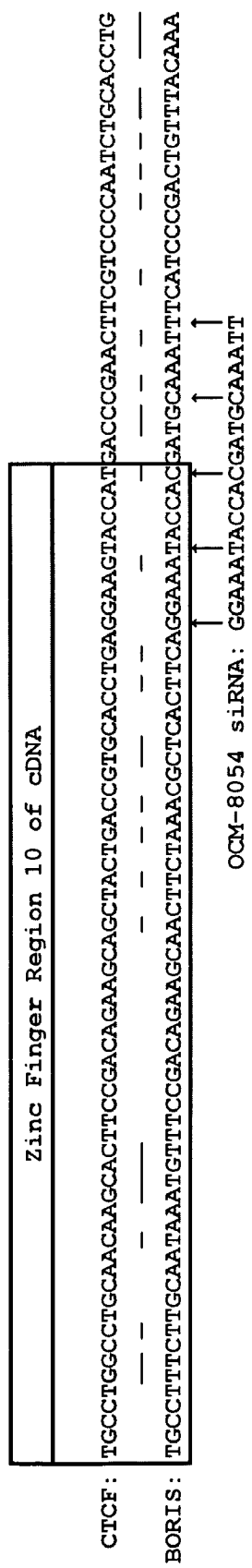
FIG. 1 is a diagram illustrating OCM-8054 (SEQ ID NO:59) siRNA targeting BORIS mRNA in zinc-finger region 10 (SEQ ID NO:128) as compared to paralogous CRCF(SEQ ID NO:129).

It is to be understood that both the foregoing general description and the following detailed description are exemplary and explanatory only and are not restrictive of the invention, as claimed. It must be noted that, as used herein and in the appended claims, the singular forms include plural referents; the use of "or" means "and/or" unless stated otherwise. Thus, for example, reference to "a subject polypeptide" includes a plurality of such polypeptides and reference to "the agent" includes reference to one or more agents and equivalents thereof known to those skilled in the art, and so forth. Moreover, it must be understood that the invention is not limited to the particular embodiments described, as such may, of course, vary. Further, the terminology used to describe particular embodiments is not intended to be limiting, since the scope of the present invention will be limited only by its claims.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Unless otherwise defined, all technical and scientific terms used herein have the same meaning as commonly understood by one of ordinary skill in the art to which this invention belongs. Suitable methods and materials are described below, however methods and materials similar or equivalent to those described herein can be used in the practice of the present invention. Thus, the materials, methods, and examples are illustrative only and not intended to be limiting. All publications, patent applications, patents, and other references mentioned herein are incorporated by reference in their entirety. In case of conflict, the present specification, including definitions, will control.

Standard techniques may be used for recombinant DNA, oligonucleotide synthesis, tissue culture and transfection (e.g., electroporation, lipofection, etc.). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)); Current Protocols in Molecular Biology (eds. Ausubel, et al., Greene Publ. Assoc., Wiley-Interscience, NY); Harlow and Lane, Antibodies, A Laboratory Manual, Cold Spring Harbor Laboratory, Cold Spring Harbor, N.Y. (1988)) the entire contents of which are incorporated herein by reference for any purpose. Unless specific definitions are provided, the nomenclatures utilized in connection with, and the laboratory procedures and techniques of, analytical chemistry, synthetic organic chemistry, and medicinal and pharmaceutical chemistry described herein are those well known and commonly used in the art. Standard techniques may be used for chemical syntheses, chemical analyses, pharmaceutical preparation, formulation, and delivery, and treatment of patients Definitions "About" as used herein means that a number referred to as "about" comprises the recited number plus or minus 1-10% of that recited number. For example, "about" 100 nucleotides can mean 100 nucleotides, 99-101 nucleotides, or up to as broad a range as 90-100 nucleotides. Whenever it appears herein, a numerical range such as "1 to 100" refers to each integer in the given range; e.g., "1 to 100 nucleotides" means that the nucleic acid can contain only 1 nucleotide, 2 nucleotides, 3 nucleotides, etc., up to and including 100 nucleotides.

"BORIS" or "the Brother of the Regulator of Imprinted Sites" protein, as used herein, refers to an epigenetically-acting zinc finger polypeptide present in mammalian testes and cancer cells, with an amino acid sequence that has greater than about 80% amino acid sequence identity, typically greater than 85% identity, often greater than 90% identity, and preferably 91%, 92%, 93%, 94%, 95%, 96%, 97%, 98% or 99% or greater amino acid sequence identity, to the BORIS amino acid sequence detailed in GenBank Accession No. AAM28645 (posted May 16, 2002). Implicitly encompassed by this definition are splice variants, variants containing conservative amino acid substitutions, and polymorphic variants capable of transforming a mammalian cell. The skilled artisan will be aware of methods for determining whether a polymorphic variant of BORIS is capable of transforming a mammalian cell, such as by transfection of a nucleic acid encoding the variant into a cell and e.g. observing colony formation. Typically, cancer cells that express BORIS have the amino acid sequence of GenBank Accession No. AAM28645, a splice variant thereof, a variant containing one or more conservative amino acid substitutions, or a polymorphic variant thereof that is capable of transforming a mammalian cell.

Identity is determined over a region of at least 20, 50, 100, 200, 500, or more contiguous amino acids. The terms "identical" or percent "identity," as used herein in the context of two or more nucleic acids or amino acid sequences, refer to two or more sequences or subsequences that are the same or have a specified percentage of amino acid residues or nucleotides that are the same when compared and aligned for maximum correspondence over a comparison window (i.e.

region). The definition includes sequences that have deletions, insertions and substitutions and may also be applied to the complement of a sequence (e.g. "100% complementary" polynucleotides). Preferably, identity is measured over the length of the polynucleotide or polypeptide, but is typically measured over a region that is at least about 20 amino acids or nucleotides in length, and often over a region that is at least 50-100 amino acids or nucleotides in length.

To calculate percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value, which is usually rounded to the nearest integer. It will be appreciated that the length of the aligned region can be a portion of one or both sequences up to the full-length of the shortest sequence. It will be appreciated that a single sequence can align differently with other sequences and hence, can have different percent sequence identity values over each aligned region.

The alignment of two or more sequences to determine percent sequence identity can be performed manually, by visual alignment, or can use computer programs that are well known in the art. For example, the algorithm described by Altschul et al. (1997, Nucleic Acids Res., 25:3389 402) can be used. This algorithm is incorporated into BLAST (basic local alignment search tool) programs, available at ncbi.nlm.nih.gov on the World Wide Web. BLAST searches can be performed to determine percent sequence identity between a nucleic acid molecule or polypeptide of the invention and any other sequence or portion thereof.

"BORIS gene" or "BORIS polynucleotide" refer to a polynucleotide sequence encoding a BORIS polypeptide, which is transcribed into an mRNA with at least about 80% nucleotide sequence identity, typically greater than 85% identity, often greater than 90% identity, and preferably 91%, 92%, 93%, 94%, 95%, 96%, 97%, 98% or 99% or greater nucleotide sequence identity to the BORIS cDNA sequence of GenBank Accession No. AF336042 (posted May 16, 2002).

BORIS nucleic acid sequences also implicitly encompass "splice variants." Similarly, BORIS polypeptides implicitly encompass any protein encoded by a splice variant of a BORIS nucleic acid. "Splice variant," as used herein, refers to the products of alternative splicing of a gene. After transcription, an initial nucleic acid transcript may be spliced such that alternate nucleic acids are produced from the same template. Mechanisms for the production of splice variants include alternate splicing of exons. Alternate polypeptides derived from the same nucleic acid by read-through transcription are also encompassed by this definition. Any products of a splicing reaction, including recombinant forms of the splice products, are included in this definition.

"CTCF" as used herein refers to CCCTC-binding factor, a paralog of BORIS that is expressed in normal mammalian cells, and which typically has about 66% amino acid sequence identity to BORIS. "CTCF gene" refers to a polynucleotide sequence encoding a CTCF polypeptide, which is transcribed into an mRNA have a nucleotide sequence that has at least at least about 80% nucleotide sequence identity, typically greater than 85% identity, often greater than 90% identity, and preferably 91%, 92%, 93%, 94%, 95%, 96%, 97%, 98% or 99% or greater nucleotide sequence identity to the CTCF cDNA sequence of GenBank Accession No.:NM_006565 (posted Jul. 20, 2008) or.

The terms "polynucleotide," "nucleic acid," and "nucleic acid molecule," are used interchangeably herein to refer to polymeric forms of nucleotides of any length. The polynucleotides can contain deoxyribonucleotides, ribonucleotides, and/or their analogs. Polynucleotides can have any three-dimensional structure, and can perform any function, known or unknown. The term polynucleotide includes single-stranded, double-stranded, and triple helical molecules, and encompasses nucleic acids containing nucleotide analogs or modified backbone residues or linkages, which can be synthetic, naturally occurring, or non-naturally occurring, and which have similar binding properties as the reference nucleic acid. In particular, interfering RNAs (e.g., siRNA, shRNA) of the invention, can contain modifications or may incorporate analogs provided these do not interfere with the ability of the interfering RNA to inactivate homologous mRNA. Examples include replacement of one or more phosphodiester bonds with phosphorothioate linkages; modifications at the 2'-position of the pentose sugar in RNA, such as incorporation of 2'-O-methyl ribonucleotides, 2'-H ribonucleotides, 2'-deoxy-2'-fluoro ribonucleotides (e.g. 2'-deoxy-2'-fluorouridine), or 2'-deoxy ribonucleotides; incorporation of universal base nucleotides, 5-C-methyl nucleotides, inverted deoxyabasic residues, or locked nucleic acid (LNA), which contains a methylene linkage between the 2' and the 4' position of the ribose.

Exemplary embodiments of polynucleotides include, without limitation, genes, gene fragments, exons, introns, mRNA, tRNA, rRNA, interfering RNA, siRNA, shRNA, miRNA, anti-sense RNA, ribozymes, cDNA, recombinant polynucleotides, branched polynucleotides, plasmids, vectors, isolated DNA of any sequence, isolated RNA of any sequence, nucleic acid probes and primers.

"Oligonucleotide" refers generally to polynucleotides that are between 5 and about 100 nucleotides of single- or double-stranded DNA. For the purposes of this disclosure, the lower limit of the size of an oligonucleotide is two, and there is no upper limit to the length of an oligonucleotide. Oligonucleotides are also known as "oligomers" or "oligos" and can be prepared by any method known in the art including isolation from naturally-occurring polynucleotides, enzymatic synthesis and chemical synthesis.

The terms "polypeptide," "peptide" and "protein" are used interchangeably herein to refer to a polymer of amino acid residues of any length. Polypeptides can have any three-dimensional structure, and can perform any function, known or unknown. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "conservatively modified variants" or "conservative variants" applies to both amino acid and nucleic acid sequences. With respect to particular nucleic acid sequences, conservatively modified variants refers to those nucleic acids which encode identical or substantially identical amino acid sequences; or for nucleic acids that do not encode an amino acid sequence, to nucleic acids that are substantially identical. As used herein, "substantially identical" means that two amino acid or polynucleotide sequences differ at no more than 10% of the amino acid or nucleotide positions, typically at no more than 5%, often at more than 2%, and most frequently at no more than 1% of the of the amino acid or nucleotide positions.

Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the alternate alanine codons without altering the encoded polypeptide. Such nucleic acid variations are "silent variations," which are one type of conservatively modified variants. Nucleic acid sequences encoding polypeptides described herein also encompass every possible silent variation of the nucleic acid. The skilled artisan will recognize that each amino acid codon in a nucleic acid (except AUG, which is ordinarily the only codon for methionine, and TGG, which is ordinarily the only codon for tryptophan) can be varied at one or more positions to code for the same amino acid. Accordingly, each silent variation of a nucleic acid that encodes a polypeptide is implicit in each described sequence with respect to the expression product.

"Complementarity" refers to the ability of a nucleic acid to form hydrogen bond(s) with another polynucleotide sequence by either traditional Watson-Crick or other non-traditional types of base pairing. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, RNA interference, antisense or triple helix inhibition. Determination of binding free energies for nucleic acid molecules is well known in the art. "Percent complementarity" refers to the percentage of contiguous residues in a nucleic acid molecule that can form hydrogen bonds (e.g., Watson-Crick base pairing) with another nucleic acid molecule. "Perfectly complementary" or "100% complementarity" means that all the contiguous nucleotides of a nucleic acid molecule will hydrogen bond with the same number of contiguous residues in a second nucleic acid molecule. "Substantial complementarity" and "substantially complementary" as used herein indicate that two nucleic acids are at least 90% complementary, typically at least 95% complementary, often at least 98% complementary, and most frequently at least 99% complementary over a region of more than about 15 nucleotides and more often more than about 19 nucleotides.

"Homology" is an indication that two nucleotide sequences represent the same gene or a gene product thereof, and typically means that that the nucleotide sequence of two or more nucleic acid molecules are partially, substantially or completely identical. When from the same organism, homologous polynucleotides are representative of the same gene having the same chromosomal location, even though there may be individual differences between the polynucleotide sequences (such as polymorphic variants, alleles and the like). In certain embodiments, a homolog can be found in a non-native position in the genome, e.g. as the result of translocation. Isolated and/or synthetic polynucleotides of the invention may be selected or designed to be homologous to an mRNA product of a gene. Preferably, homologous interfering RNAs of the invention are substantially identical to a target genomic DNA or mRNA sequence, but sufficiently different from other sequences in the genome so that they do not elicit an RNA interference effect with off-target polynucleotides.

Regarding amino acid sequences, one of skill in the art will recognize that individual substitutions, deletions or insertions to a nucleic acid, peptide, polypeptide, or protein sequence which alters, inserts or deletes a single amino acid or a small percentage of amino acids in the encoded sequence is a "conservatively modified variant" where the alteration results in the substitution of an amino acid with a chemically similar amino acid. Conservative substitution tables detailing functionally similar amino acids are well known in the art. Such conservatively modified variants are in addition to and do not exclude functionally equivalent polymorphic variants, homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "RNA interference" or "RNAi" is broadly defined herein to include all posttranscriptional mechanisms of double-strand RNA mediated inhibition of gene expression. RNAi includes mechanisms that utilize siRNA and shRNA, as well as longer forms of duplex RNA. RNA interference is used to inhibit the function of an endogenous gene product, and thus mimic the effect of a loss-of-function mutation.

A "small interfering RNA" or "siRNA" is a double-stranded polynucleotide (e.g. RNA) molecule that mediates inhibition of the expression of a gene with which it shares homology when present in the same cell as the gene (i.e., target gene). siRNAs of the invention inhibit gene expression by directing cleavage of the target region of a homologous polynucleotide.

The region of the gene or other nucleotide sequence over which there is homology is known as the "target region." siRNA thus refers to the double-stranded polynucleotides formed by short, complementary strands of polynucleotide. The complementary regions of nucleic acid sequence that hybridize to form duplex polynucleotide molecules typically have substantial or complete complementarity to each other and are homologous to a target region of a gene (e.g., the BORIS gene). In one embodiment, an siRNA refers to a nucleic acid that has substantial or complete identity to a target gene and forms a double-stranded oligonucleotide.

Typically, siRNAs of the invention are at least about 15-30 nucleotides in length, (e.g., each complementary polynucleotide of the double-stranded siRNA is 15-30 nucleotides in length, and the double-stranded siRNA is about 15-30 base pairs in length), typically about 19-24 nucleotides in length, most frequently about 21-22 nucleotides in length.

Endogenous siRNAs are produced from cleavage of longer double-strand RNA precursors by an RNaseIII endonuclease and have a characteristic 2 nucleotide 3' overhang that allows them to be recognized by RNAi machinery, ultimately leading to homology-dependent cleavage of the target mRNA region. Cleavage is reportedly effected between bases 10 and 11 relative to the 5' end of the antisense siRNA strand. Rules that govern selectivity of siRNA utilization by endogenous RNAi machinery are based upon differential thermodynamic stabilities of the ends of the siRNAs, with less thermodynamically stable ends favored. Such information can be valuable in selecting siRNA sequences from a target mRNA, which are then assessed for RNA interference activity according to the methods of the invention.

Partial complementarity between an siRNA and target mRNA may in certain cases repress translation or destabilize the transcripts if binding of the siRNA mimics microRNA (miRNA) interactions with their target sites. MicroRNAs are endogenous substrates for the RNAi machinery. Micro RNAs are initially expressed as long primary transcripts (pri-miR-NAs), which are processed within the nucleus into 60-70 by hairpins. The loop is removed by further processing in the cytoplasm by an RNase III activity. Mature miRNAs share only partial complementarity with sequences in the 3'UTR of target mRNAs. The primary mechanism of action of miRNAs is translational inhibition, although this can be accompanied by message degradation.

"Expression" or "gene expression" as used herein refers to the conversion of the information from a gene into a gene product. A gene product can be the direct transcriptional product of a gene (e.g., mRNA, tRNA, rRNA, antisense RNA, ribozyme, structural RNA, or any other type of RNA) or a protein produced by translation. According to the methods of the present invention, BORIS gene expression is typically measured by determining the amount BORIS polypeptide in the cell, such as by enzyme linked immunosorbent assay (ELISA), Western blotting, radioimmunoassay (RIA), immunefluorescence, fluorescence activated cell analysis (FACS) or other methods that utilize anti-BORIS antibodies. BORIS gene expression may also be detected using biochemical techniques for analyzing RNA such as Northern blotting, nuclease protection assays, reverse transcription, microarray hybridization, and the like, which are well known in the art. In other aspects of the invention, BORIS expression is determined by measuring an activity of BORIS, such as BORIS methylation activity, DNA binding activity, or cell transformation activity. In certain embodiments of the invention, the downstream effects of reduced BORIS gene expression may be measured as an indication of the inhibition of BORIS expression. Such downstream effects include reduced cell viability, cell death, increased apoptosis or the increased activity of apoptosis-related markers.

The terms "silencing," "inhibition," and "knockdown" of gene expression are used interchangeably herein to refer to a reduction in the amount of a BORIS gene product (i.e. BORIS polypeptide or BORIS mRNA) in a cell as a result of RNA interference. Inhibition indicates that expression of BORIS is reduced by 1-100% (e.g., 10%, 20%, 30%, 40%, 50%, 60%, 70%, 80%, 90%, 95%, or 99% reduced) compared to expression of BORIS in the absence of RNA interference.

As used herein, "sense" strand of an oligo- or polynucleotide refers to a molecule having a nucleotide sequence that is homologous to target mRNA strand, which target mRNA strand codes for a protein. In some embodiments, a sense strand is 100% identical to a sequence of the target mRNA. In other embodiments, a sense strand may be about 90%, about 95%, or about 99% identical to a target mRNA. An "antisense" strand refers to the complement of a sense strand or a target mRNA. In some embodiments, sense and antisense strands are 100% complementary to each. In other embodiments, the duplex polynucleotide, such as an siRNA, may contain one or more mismatched base pairs or terminal overhangs.

"Antibody" or "antibodies", as used herein, include naturally occurring species such as polyclonal and monoclonal antibodies as well as any antigen-binding portion, fragment or subunit of a naturally occurring molecule, such as for example Fab, Fab', and F(ab)$_2$ fragments of an antibody. Also contemplated for use in the methods of the invention are recombinant, truncated, single chain, chimeric, and hybrid antibodies, including, but not limited to, humanized and primatized antibodies, and other non-naturally occurring antibody forms.

A "ligand" is any molecule that binds to a specific site on another molecule, often a receptor.

The terms "patient," "subject," and "individual," are used interchangeably herein, to refer to mammals, including, but not limited to, humans, murines, simians, felines, canines, equines, bovines, porcines, ovines, caprines, avians, mammalian farm and agricultural animals, mammalian sport animals, and mammalian pets.

"Biological sample," as used herein, includes biological fluids such as blood, serum, plasma, urine, cerebrospinal fluid, tears, saliva, lymph, dialysis fluid, lavage fluid, semen, and other liquid samples or tissues of biological origin. It includes cells or cells derived therefrom and the progeny thereof, including cells in culture, cell supernatants, and cell lysates. It includes organ or tissue culture-derived fluids, tissue biopsy samples, tumor biopsy samples, stool samples, and fluids extracted from physiological tissues. Cells dissociated from solid tissues (e.g. tumors), tissue sections, and cell lysates are included. The definition also includes samples that have been manipulated in any way after their procurement, such as by treatment with reagents, solubilization, or enrichment for certain components, such as polynucleotides or polypeptides. Also included in the term are derivatives and fractions of biological samples. A biological sample can be used in a diagnostic or monitoring assay, and may be analyzed for BORIS expression products.

"Treatment," as used herein, covers any administration or application of remedies for disease in an animal, including a human, and includes inhibiting the disease, i.e., arresting its development; relieving the disease, i.e., causing its regression; and eliminating the disease, i.e., causing the removal of diseased cells or restoration of a non-diseased state.

"Cancer" as used herein, refers to any abnormal cell or tissue growth, e.g., a tumor, which can be malignant or non-malignant. Cancer is characterized by uncontrolled proliferation of cells that may or may not invade the surrounding tissue and, hence, may or may not metastasize to new body sites. Cancer encompasses carcinomas, which are cancers of epithelial cells (e.g. squamous cell carcinoma, adenocarcinoma, melanomas, and hepatomas). Cancer also encompasses sarcomas, which are tumors of mesenchymal origin, (e.g. osteogenic sarcomas, leukemias, and lymphomas). Cancers can involve one or more neoplastic cell type.

A "pharmaceutical composition" or "pharmaceutically acceptable composition" of modulators, polypeptides, or polynucleotides herein refers to a composition that usually contains a pharmaceutically acceptable carrier or excipient that is conventional in the art and which is suitable for administration into a subject for therapeutic, diagnostic, or prophylactic purposes. For example, compositions for oral administration can form solutions, suspensions, tablets, pills, capsules, sustained release formulations, oral rinses, or powders.

siRNA Inhibition of BORIS

The present invention is based on the observation that short interfering RNAs (siRNAs) are effective in inhibiting the expression of the Brother of the Regulator of Imprinted Sites (BORIS). Thus, the present invention provides methods for inhibiting expression of BORIS in a cell through the process of RNA interference. According to one aspect of the invention, small interfering RNA (siRNA) molecules that direct cleavage of a BORIS mRNA are introduced into a cell that expresses a BORIS polypeptide, and the resulting cleavage of BORIS mRNA inhibits expression of BORIS in the cell.

As detailed below under "EXAMPLES", concentrations as low as the nanomolar range were effective in inhibiting BORIS gene expression. Accordingly, the present invention contemplates using siRNA at concentrations of 0.001 nM to greater than 50 µM; typically 0.01 nM to 5 µM; frequently 0.1 nM to 500 nM; and most often 1 nM to 50 nM.

The inhibition of expression of BORIS in the cell by the RNAi methods of the invention typically results in at least about 10% inhibition (relative to the amount of BORIS in an untreated, control cell) within 1-5 days. In certain embodiments, at least about 20%, 40%, 60%, 80%, 90% or 95% inhibition of BORIS expression is obtained. In some embodiments of the invention, at least about 50-90% inhibition, at least about 60-95% inhibition, or at least about 70-99% inhibition of BORIS expression is observed. The percent inhibition of BORIS expression in a cell is typically determined by measuring the amount of BORIS polypeptide in a cell treated with an siRNA as compared to the amount of BORIS polypeptide in an untreated control cell. Any method can be used to measure BORIS polypeptide, such as immunological methods e.g. western blotting, enzyme linked immunoassays (ELISAs), immunoprecipitation, immunofluorescence, FACS and other methods involving anti-BORIS antibodies or the like. BORIS gene expression may also be detected using biochemical techniques for analyzing RNA (e.g., mRNA) such as Northern blotting, nuclease protection assays, reverse transcription, and microarray hybridization, In other aspects of the invention, BORIS expression is determined by measuring an activity of BORIS, such as BORIS methylation activity, DNA binding activity, or cell transformation activity. In certain embodiments of the invention, the downstream effects of reduced BORIS gene expression may be measured as an indication of the inhibition of BORIS expression. Such downstream effects include reduced cell viability, cell death, increased apoptosis or the increased activity of apoptosis-related markers (e.g. caspases).

Any region of the BORIS nucleic acid sequence can be used as a target for designing the siRNAs of the invention, particularly regions of the mRNA sequence disclosed in GenBank under Accession Number AF336042 (deposited May 16, 2002). Preferably, the siRNA will be substantially identical to a BORIS nucleic acid sequence over a stretch of at least 10, 11, 12, 13, 14, 15, 16, 17, 18, 19, 20, 21, or 22 nucleotides. Typically, the target region is an exonic region that is towards the 5' end of the targeted BORIS mRNA. A preferred target region of BORIS is the 11 zinc finger DNA binding region.

In certain embodiments, the siRNA is homologous to a 15-30 nucleotide target region of BORIS polynucleotide. Polynucleotide sequences suitable for siRNAs of the invention are set forth as SEQ ID NOs:1-61. In certain embodiments, sequences suitable for siRNAs of the invention are set forth as SEQ ID NOs:62-123. In one embodiment of the invention, the siRNA comprises OCM-8054 (SEQ ID NO:59). In another embodiment, the siRNA comprises OCM-8055 (SEQ ID NO:60).

In certain embodiments of the invention, the siRNAs are double-stranded RNAs, at least about 15-30 nucleotides in length, e.g., each complementary polynucleotide of the double-stranded siRNA is 15-30 nucleotides in length, and the double-stranded siRNA is about 15-30 base pairs in length, typically about 19-24 base nucleotides, most frequently about 21-22 nucleotides in length, that are prepared from chemically synthesized oligonucleotides and then introduced directly into the cell, e.g. by transfection. In some embodiments of the invention, the siRNA is a DNA-RNA chimera (having both ribo- and deoxyribonucleotides on a single oligonucleotide strand) or a DNA-RNA hybrid (in which one strand is DNA and the other is RNA).

The double-strand siRNAs of the invention may be blunt ended or have single nucleotide 5' overhangs at one or both 5' termini. However, it is known that the most potent silencing induced by administration of double-stranded RNA occurs when the duplexes have overhanging 3' ends of 1-3 nucleotides. Thus, the siRNAs of the invention typically have overhangs at one or preferably both of its 3' termini, these overhangs are preferably only a few nucleotides in length and in particular are one or two nucleotides in length, preferably two nucleotides in length. To provide an example, but not a limitation on the siRNA molecules of the invention, 21 nucleotide oligonucleotides that form a 19 nucleotide duplex region of base pairs with 2 nucleotide 3'-overhangs are very potent at stimulation of RNA interference. In certain embodiments, siRNAs of the invention have a 19 ribonucleotide duplex region with 2 deoxyribonucleotide 3' overhangs on each end.

Chemically synthesized oligonucleotides suitable for use in the present invention can be prepared by any method known in the art. To increase the stability and/or improve the efficacy of the oligonucleotides in RNAi methods, modifications of the sugar, base or phosphodiester backbone can be incorporated. Non-limiting examples of such modifications include replacement of one or more phosphodiester bonds with phosphorothioate linkages; modifications at the 2'-position of the pentose sugar, such as incorporation of 2'-O-methyl ribonucleotides, 2'-H ribonucleotides, 2'-deoxy-2'-fluoro ribonucleotides (e.g. 2'-deoxy-2'-fluorouridine), or 2'-deoxy ribonucleotides; incorporation of universal base nucleotides, 5-C-methyl nucleotides, inverted deoxyabasic residues, or locked nucleic acid (LNA), which contains a methylene linkage between the 2' and the 4' position of the ribose. Additional chemical modifications of siRNA molecules contemplated for use in the present invention are described in Corey (J. Clin. Invest. (2007) 12:3615-22), the contents of which are incorporated by reference herein); other suitable modifications will be well known to the skilled artisan. Such chemical modifications, when incorporated into the strands of double-stranded RNA, have been shown to potentiate or preserve the ability to induce RNA interference in the target cells while at the same time, dramatically increasing the serum stability of the molecules.

Alternatively, template polynucleotides can be prepared that encode the "sense" and "anti-sense" strand of the siRNA molecules of the invention. In certain aspects, the template polynucleotides of the invention are used to enzymatically synthesize the complementary strands of the siRNA in vitro. In other aspects, the polynucleotide can be, for example, transfected into a cell for intracellular synthesis of the siRNA. In these aspects of the invention, introduction of siRNA into the cell is indirect in that a template polynucleotide is introduced into a cell, which then serves as a template for synthesis of the siRNA strands using cellular machinery, but has the effect of introducing siRNA into the cell.

Accordingly, the present invention provides template polynucleotides for directing synthesis of interfering RNAs both in vitro and in vivo. In certain embodiments of the invention, the template polynucleotides encode the complementary strands of siRNAs, which are not greater than 30 nucleotides in length, are typically are 19-24, and frequently 21-22 nucleotides in length. Such template polynucleotides are particularly useful for in vitro synthesis of siRNA oligonucleotides. The skilled artisan will be knowledgeable in recombinant DNA methods for constructing polynucleotides that can be transcribed in vitro to produce the desired oligonucleotide products.

In other embodiments, the polynucleotides of the invention encode siRNA precursors, such as the complementary strands of longer double-strand interfering RNA molecules, or short hairpin RNAs (shRNAs), which mimic naturally occurring precursor microRNAs (miRNAs) and are efficiently processed by the mammalian cellular machinery into active siRNA. While not wishing to be bound by a particular theory, miRNAs are believed to be endogenous substrates for the RNAi machinery, which are initially expressed as long primary transcripts (pri-miRNAs), and then processed into 60-70 by hairpins. Finally, the loop of the hairpin is removed resulting in siRNAs.

Thus, the present invention also provides polynucleotide templates for shRNA as well as templates for one or both strands of an siRNA. The shRNA templates typically include a promoter directly followed by at least about 18 nucleotides, typically 19, 20, 21 or 22 nucleotides, of sense (or antisense) target sequence, a 4-13 nucleotide loop, the complementary antisense (or sense) target sequence and finally a stretch of at least four to six U's as a terminator. The sense and anti-sense sequences are complementary but may not be completely symmetrical, as the hairpin structure may contain 3' or 5' overhang nucleotides (e.g., 1, 2, 3, 4, or 5 nucleotide overhangs). Similar templates for siRNAs can be produced, for example, by placing sense and antisense target sequences under the control of their own promoters in the same construct, without an intervening loop.

The promoter will be operably linked to the region encoding the siRNA, shRNA or other interfering RNA. Typically, the RNA coding sequences will be immediately downstream of the transcriptional start site or be separated by a minimal distance such as less than about 20 base pairs, typically less than about 10 base pairs, frequently less than about 5 base pairs and most often 2 two or fewer base pairs. "Operably linked," as used herein, means without limitation, that the RNA coding region is in the correct location and orientation with respect to the promoter such that expression of the gene will be effected when the promoter is contacted with the appropriate polymerase and any required transcription factors.

The promoter may be any suitable promoter for directing transcription of the shRNA or siRNA. In certain embodiments, the promoter is an RNA polymerase III (pol III) promoter. A suitable range of RNA polymerase III promoters are described, for example, in Paule & White (Nucleic Acids Res. (2000) 28:1283-98), which is incorporated by reference herein in its entirety. RNA polymerase III promoters include any naturally occurring, synthetic or engineered DNA sequence that can direct RNA polymerase III to transcribe downstream RNA coding sequences. The RNA polymerase III promoter or promoters used in the constructs of the invention can be inducible. Particularly suitable pol III promoters include those from H1 RNA, 5S, U6, adenovirus VA1, Vault, telomerase RNA, and tRNA genes, as well as the tetracycline responsive promoters described in Ohkawa & Taira (Human Gene Ther. (2001) 11:577-85) and in Meissner et al. (Nucleic Acids Res., (2001) 29:1672-82), which are incorporated herein by reference.

In other embodiments, the promoter is recognized by RNA polymerase II (pol II). A wide variety of pol II promoters are known in the art, including many cell-specific and inducible promoters. Use of such cell-specific and inducible promoters may be desirable as a mechanism for limiting RNAi effects to a particular cell type or controlling the timing of expression.

The template polynucleotides of the invention can be cloned into vectors, including but not limited to plasmid, cosmid, phagemid, and viral vectors according to well-known methods. The vectors can then be introduced into target cells that express BORIS where e.g, the siRNA produced therefrom directs cleavage of BORIS mRNA and thereby inhibits BORIS expression. The skilled artisan will appreciate that bacterial, bacteriophage, insect, fungal and other non-mammalian vectors may provide suitable templates for introduction into cultured mammalian cells. For clinical applications, a vector capable of persistence in the target cell, such as a viral vector, may be more desirable. Viral vectors also offer the advantage of efficient transfer of the template polynucleotide into the cell via infection rather than transfection. Exemplary viral vectors for clinical applications of the invention include but are not limited to adenoviruses, adeno-associated viruses, retroviruses, lentiviruses, vaccinia viruses, herpes viruses, and papilloma viruses.

In yet another embodiment, siRNAs suitable for use in the invention can be prepared by enzymatic digestion of a longer double-strand RNA using an RNase III type enzyme (e.g., Dicer). Commercially available Dicer siRNA generation kits are currently available, permitting synthesis of large numbers of siRNAs from full length target genes (Gene Therapy Systems, Inc, MV062603).

Effects of Silencing BORIS Gene Expression siRNA generated to the zing-finger number 10 region of BORIS resulted in inhibition of BORIS protein expression in the MDA-MB-231 estrogen receptor negative breast cancer cell line, as detailed below under "EXAMPLES." Inhibition of BORIS gene expression correlated with induction of cell death and activation of DEVD-recognizing caspases, suggesting an apoptotic mechanism for the cell death. The observed results were specific for BORIS inhibition because the same siRNA was not toxic to control non-malignant epithelial cells that do not express BORIS.

Therefore, the present invention may be useful for treating cancer in a subject, such as a mammal, where the cancer cell expresses BORIS. In certain embodiments the cancer cell is a human cell and the subject is a human patient. The cancer cell can be present in a primary tumor, or in metastases to other tissues or organs. BORIS has been detected in a wide variety of cancer types, and therefore methods of the invention may be useful for treating, e.g. breast, lung, skin, bone, brain, colon, prostate, pancreas, mast cell, ovarian, uterine and other cancer cells.

Indeed, BORIS expression was effectively targeted for inhibition by siRNA in glioblastoma multiforme cells (see Example 5, below). As in the breast cancer cell type, treatment of glioblastoma, (brain-derived cancer cells) resulted in apoptotic cell death, but did not affect normal cells.

Surprisingly, however, the same siRNA effective for inhibiting BORIS expression in breast cancer (OCM-8054; SEQ ID NO:59) was not effective in the glioblastoma cell line. Instead, BORIS siRNAcontaining OCM-8055(SEQ ID NO:60) was found to be effective in this cell type.

The difference in efficacy of siRNAs between breast and glioblastoma cancer cells appears to result from the expression of variant forms of BORIS, particularly splice variants, in different cancer types (see Example 6, below). Thus, in the methods of the present invention, it may be necessary to analyze the BORIS mRNAs transcribed prior to selecting an siRNA sequence for inhibiting BORIS expression in a particular cancer. This can be accomplished, for example, by analyzing BORIS transcripts for splice variants by PCR. According to this aspect of the invention, mRNA isolated from a biological sample containing cancer cells is contacted with one or more primer pairs, such as a series of primer pairs that selectively amplify overlapping fragments of the BORIS gene. Alternatively, the splice variant profile of BORIS mRNA in a particular cancer can be detected using Northern blotting, primer extension, nuclease protection or other methods well known in the art. The results of the mRNA profiling are then compared against the position of homologous BORIS siRNA sequences, such as the sequences set forth in SEQ ID NOs:1-61 and/or 62-123. An siRNA that targets a region present in mRNA from the cancer is selected for inhibiting BORIS gene expression and is introduced into the cancer cells.

Alternatively, two or more siRNAs with demonstrated efficacy for inhibiting BORIS expression can be simultaneously or sequentially introduced into the cancer cells. This may be a prudent approach for especially fast growing or virulent forms of cancer. The present invention contemplates that a cocktail of siRNAs homologous to target regions along the length of BORIS can be prepared for first-line treatment of such cancers. Conveniently, polynucleotides can be generated that express multiple siRNAs from a single template.

Introduction of siRNA into Cells

The siRNAs of the invention and constructs suitable for use in effecting intracellular production of interfering RNA, can be introduced into the cell by any method known in the art. Methods for delivery to cells in vitro include, without limitation, transfection, infection, electroporation and the like. These same methods can be used to deliver siRNA or template polynucleotides to cancer cells in a patient.

When introduction is by transfection, various transfection agents can be added to improve the efficiency of transfection. Such agents include cationic compounds, particularly lipids, phospholipids, cationic lipids and cationic polymers, e.g. natural polymers including chitosan and atelocollagen, and synthetic polymers including poly(L-lysine), PEI, and dendrimers; poly(ethylene glycol) (PEG); DOTAP; Lipofectamine™, AtuFECT01/DphPE; LIC-101; 2-O-(2-diethylaminoethyl)-carbamoyl-1; lipiodol; 3-O-dioleoylglycerol; phosphatidylcholine; D1inDMA; DSPC; cholesterol; nanoparticles; liposomes of various types including cationic liposomes, PEG liposomes, and galactosylated liposomes, DOPC liposomes, and liposomes containing PEG-CDMA.

In a subject, the RNA interference polynucleotides of the invention can be administered systemically (e.g., intravenously, orally, etc.) or directly to the tumor tissue (e.g., via intratumor injection, aerosol administration to the lung, dermal application to the skin) in a pharmaceutically acceptable composition. Delivery can be effected using the techniques and reagents described herein, including transfection agents, liposome formulations, nanoparticles and the like. Hydrodynamic administration (e.g. administration of siRNA intravenously in a large volume under pressure) can also be used as a local or systemic method to deliver the polynucleotide of the invention to tumors. In one embodiment, for example, hydrodynamic administration can be accomplished by isolating blood vessels that feed and drain a particular tumor for local application of siRNA under fluid pressure.

The siRNA and template polynucleotides of the present invention can also be conjugated or complexed to macromolecules or polymers such as cholesterol, PEG, or polypeptides to increase the stability, reduce systemic clearance or promote cell-specific targeting in a patient. Polyethylenimine (PEI) is an example of a suitable cationic polymer for in vivo administration. Varying sizes of PEI can be used, including linear 22 kDa and branched 25 kDa PEI (other sizes, modified and unmodified, as well as biodegradable versions can be used). Conjugation of cholesterol to the 3' end of the sense strand of 2'-OH siRNA by means of a synthetic pyrrolidone linker (chol-siRNA) has been reported as a means for increasing the stability of siRNA in vivo. An amino acid sequence from a rabies glycoprotein has also been used to both stabilize and target siRNA to specific receptor-containing cells in the brain following intravascular injection (Kumar et al., Nature (2007) 448:39-43). The skilled artisan will appreciate that similar strategies can be developed to target cancer cells for use in the methods of the present invention.

The present invention also contemplates targeting to specific cell types through the use of antibody- or ligand-conjugated liposomes, microparticles or nanoparticles, which are known in the art. In this context, targeting may be less critical for the purpose of preventing toxicity to normal non-cancerous cells since the siRNA will generally be non-toxic to cells that do not express BORIS. But such methods may be useful for focusing delivery of therapeutic siRNA to cancer tissue, and thereby achieving higher concentrations with lower doses of polynucleotide.

Nanoparticles are designed to disrupt the endosomes and deliver siRNA into the cytoplasm e.g., of cancer cells. They are chemically stable at pH 7.4 but because certain ester linkages in the particles degrade into linear polymer chains and small nontoxic molecules under mildly acidic conditions, the molecular design of such nanoparticles allows them to circulate in the blood, at pH 7.4, but then rapidly hydrolyze upon endocytosis in the acidic environment of the endosomes. Furthermore, nanoparticles can be targeted to specific cell types in a manner similar to liposomes and other conjugates or vesicles.

In another embodiment of the invention, BORIS siRNA is administered to patients with lung or liver cancers due to the propensity of siRNA to localize to these sites, and the prevalence of many types of cancer to metastasize to these organs. Enhancement of localization can be induced by a variety of procedures known to those skilled in the art. For example, siRNA may be incorporated into microbubbles that burst upon exposure to ultrasound. Ultrasound may then be localized to the specific area where the tumor is present.

In yet another embodiment of the invention, BORIS siRNA is administered in combination with an inhibitor of P-glycoprotein (e.g. cyclosporin A), to patients with solid tumors that have metastasized to organs such as lung or liver. Cyclosporin A has been shown to inhibit P-glycoprotein transporters on the cell membrane that can efflux foreign material (xenobiotics) that enter cells. By suppressing these transporters of multidrug resistant cells, siRNA may more easily penetrate the cells and inhibit the production of BORIS.

Delivery can also be effected using, for example, non-toxic viral delivery systems (e.g., an adeno-associated viral delivery system). Additional techniques for the localization of siRNA to specific tissue are described, for example, in Saito et al., ((2007) J. Orthop. Res. Jun 4); Kawakami & Hashida, (Drug Metab. Pharmacokinet (2007) 22: 142-51) the entire contents of which are incorporated by reference herein. Optimum dosing will depend on the patient, the siRNA, the mode of administration, and the effect sought. Optimum conditions can be established by those skilled in the art using routine procedures.

The present invention also provides combination therapy for cancer. Thus, BORIS-directed RNA interference can be coupled with traditional surgical removal of tumor tissue, radiation therapy, immunotherapeutic treatment and/or chemotherapeutic methods for treating cancer. In one embodiment, surgical removal of a tumor is accompanied by localized instillation of the surrounding area with siRNA of the invention.

In another embodiment, an immunotherapeutic agent, such as an innate immune stimulator, a stimulator of adaptive immunity, or both an innate immune stimulator and a stimulator of adaptive immunity, is co-administered with siRNA, which can be e.g. simultaneous or sequential co-administration. The innate immune stimulator can, for example, activate immune functions through the upregulation of biological function of cells such as dendritic cells, macrophages, neutrophils, mast cells, natural killer cells, natural killer T cells, gamma delta cells, and B1 B cells. The stimulator of adaptive immunity can be, for example a peptide vaccine, a protein vaccine, an altered peptide-ligand vaccine, a DNA vaccine, an RNA vaccine, a cell therapy, or a dendritic cell vaccine. In certain aspects, the vaccine stimulates a T cell response against an epitope of the BORIS protein.

In another embodiment, RNA interference is induced in combination (e.g. sequential or simultaneous administration in a pharmaceutically acceptable composition) with at least one typical therapeutic or palliative anticancer drug, which include, without limitation alkylating agents such as thiotepa, and cyclosphosphamide; alkyl sulfonates such as, busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunomycin, daunorubicin, detorubicin, 6-diazo-5-oxo-L-norleucine, doxorubicin, epirubicin, esorubicin, idarubicin, marcellomycin, mitomycins (e.g., mitomycin C), mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mopidamol; nitracrine; pentostatin; phenamet; pirarubicin; podophyllinic acid; 2-ethylhydrazide; procarbazine; PSK; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); taxanes, paclitaxel and docetaxel; gemcitabine; platinum analogs such as cisplatin and carboplatin,; etoposide; mitoxantrone; anti-mitotics; vinblastine; vincristine; vinorelbine; novantrone; teniposide; aminopterin; ibandronate; iretotecan; topoisomerase inhibitor RFS 2000; difluoromethylomithine (DMFO); retinoic acid; esperamicins; capecitabine; abarelix; aldesleukin; aldesleukin; alemtuzumab; alitretinoin; allopurinol; amifostine; anakinra; anastrozole; arsenic trioxide; asparaginase; bcg live; bevacizumab; bexarotene; bleomycin; bortezomib; celecoxib; cetuximab; cladribine; clofarabine; dalteparin sodium; darbepoetin alfa; dasatinib; daunomycin; decitabine; denileukin; dexrazoxane; eculizumab; elliott's b solution; epoetin alfa; erlotinib; exemestane; fentanyl citrate; filgrastim; fulvestrant; gefitinib; gemtuzumab ozogamicin; goserelin acetate; histrelin acetate; ibritumomab tiuxetan; imatinib mesylate; interferon alfa 2a; irinotecan; lapatinib; ditosylate; lenalidomide; letrozole; leucovorin; leuprolide; acetate; levamisole; ccnu; meclorethamine; megestrol; acetatemesna; methoxsalen; nandrolone phenpropionate; nelarabine; nofetumomab; oprelvekin; oxaliplatin; palifermin; pamidronate; panitumumab; pegademase; pegaspargase; pegfilgrastim; peginterferon alfa-2b; pemetrexed disodium; plicamycin; mithramycin; porfimer sodium; quinacrine; rasburicase; rituximab; sargramostim; sorafenib; sunitinib; tamoxifen; thalidomide; topotecan; topotecan hcl; toremifene; tositumomab; trastuzumab; tretinoin; atra; valrubicin; vorinostat; zoledronate; zoledronic acid; decitabine; aprepitant; imiquimod; ixabepilone; letrozole; oxaliplatin; raloxifene; rituximab; sorafenib tosylate; tarabine pfs; erlotinib; nilotinib; docetaxel; temozolomide; temsirolimus; bendamustine hydrochloride; lapatinib ditosylate; leuprolide acetate; and dexrazoxane hydrochloride.

The invention will now be further exemplified by the following non-limiting examples, including the experiments conducted and results achieved, which are provided for illustrative purposes only and are not to be construed as limiting the present invention in any way.

EXAMPLES

Materials and Methods

Cell cultures and reagents. The MDA-MB-231 (human mammary gland ductal carcinoma) and ARPE-19 (human retinal pigment epithelium), HEK-293 (Human Embryonic Kidney Epithelial Cells), and U87-MG and U251 (glioblastoma multiforme) cell lines were purchased from the American Type Culture Collection (Manassas, Va.). Cell cultures were maintained at 37° C., with 5% $CO_2$ under fully humidified conditions in DMEM (Cellgro-Mediatech, Herndon, Va.) supplemented with 10% fetal bovine serum (Hy-Clone, Logan, Utah) and 1% penicillin/ streptomycin (Cellgro-Mediatech). Cells were plated in 12-well plates and harvested at ~90% confluence ($5 \times 10^5$ cells per well) for RNA.

siRNA Transfection. The cDNA sequence for human BORIS (GenBank Accession No. AF336042) was used to develop siRNAs targeting BORIS but not CTCF (GenBank Accession No. NM_006565), confirmed by manual alignment (FIG. 1) and BLAST analysis. As illustrated in FIG. 1, the OCM-8054 siRNA shares complete homology to the BORIS cDNA sequence, but not to CTCF. Double-stranded siRNAs targeting human BORIS were purchased through Ambion (Austin, Tex.). The OCM-8054 siRNA sequence is 5'-GGAAAUACCACGAUGCAAATT-3' (SEQ ID NO:59). As controls, non-targeting scrambled siRNA (cat#4611G) and siRNA-targeting GAPDH (cat#AM4624) were purchased from Ambion. Transfections with siRNA concentrations ranging from 1.7 to 50 nM were performed using Lipofectamine™ RNAiMAX cationic lipid reagent (Invitrogen, Carlsbad, Calif.) per the manufacturer's instructions.

Western blot. Cultures of human mammary gland ductal carcinoma cells (MDA-MB-231), or human retinal pigment epithelial (ARPE-19) cells were directly lysed in SDS sample buffer and subjected to electrophoresis on 10% SDS gels.

Separated proteins were subsequently transferred onto BioTrace™ NT nitrocellulose blotting membranes (PALL, Pensacola, Fla.), and target proteins were detected by incubating the membrane with the following antibodies: anti-BORIS (affinity-purified rabbit IgG; Cat. No. 600-401-907; Rockland Immunochemicals, Gilbertsville, Pa.) and peroxidase-conjugated secondary antibody (affinity-purified donkey anti-rabbit IgG; Cat. No. 611-703-127; Rockland Immunochemicals). An antibody to β-actin (mouse monoclonal IgG1; Cat. No. sc-47778; Santa Cruz Biotechnology, Santa Cruz, Calif.) was also used to verify that equal amounts of protein were loaded into each lane. A Pierce ECL enhanced chemiluminescence detection kit was used to detect bound antibodies (Thermo Fisher Scientific, Rockford, Ill.) and the membrane was exposed to Kodak® X-Omat LS film.

Cell Viability Assay. The CellTiter 96® AQueous One Solution Cell Proliferation Assay (Promega, Madison, Wis.) was used to determine cytotoxicity effects of siRNA transfection per the manufacturer's protocol. Absorbance at 490 nm was determined on a Molecular Devices (Sunnyvale, Calif.) SpectraMax M5$^e$ microplate reader. All transfections and conditions were conducted in triplicate and repeated at least twice. All values were normalized to the viability of scramble siRNA-transfected MDA-MB-231 cancer cells, which were similar to untransfected controls.

Caspase 3/7 Assay. Caspase 3/7 activation in transfected cells was measured using the Caspase-Glo® 3/7 Assay (Promega) as recommended by manufacturer at either 24- or 48-h post-transfection. As a positive control, 20 μM Hydrogen Peroxide (Sigma-Aldrich) was added for 24 h. Luminometric data, in a 96-well format, were collected using a Molecular Devices SpectraMax M5$^e$ microplate reader (Sunnyvale, Calif.). All transfections and conditions were conducted in triplicate and repeated at least twice. All values were normalized to the viability of scramble siRNA transfected MDA-MB-231 cancer cells, which were similar to untransfected controls.

Statistical analysis. The error bars in histograms of FIGS. 2-5 represent means±standard deviation (SD) and significance was calculated using ANOVA software.

Example 1

BORIS Expression in MDA-MB-231 Breast Cancer Cells

BORIS expression was measured in the MDA-MB-231 breast cancer cell line, an established in vitro system for assessment of novel cancer therapeutic approaches, especially in the area of RNAi. (Kunigal et al, Int. J. Cancer (2007) 121:2307-16; Ohri et al, Cancer Biol. Ther. (2007) Apr. 20; 6(7) (Epub ahead of print)). Using the Western blot technique, full-length 75 kDa BORIS protein was observed in lysates of MDA-MB-231, but not control human retinal pigment epithelium (ARPE-19) cells or human mammary epithelial (HMEC) cells. Expression appeared consistent and was present at various time points during passage of the cells. Furthermore, different batches of MDA-MB-231 cancer cells demonstrated a consistent level of expression.

Example 2

Silencing BORIS Expression by OCM-8054 siRNA

To determine whether RNAi induction was specifically useful for inhibition of BORIS protein, numerous oligonucleotide sequences (SEQ ID NOs:1-61) targeting various regions of the BORIS molecule were designed for use as siRNAs. siRNAs were prepared from the sequences and delivered to the MDA-MB-231 cells by the method described in Kunigal et al, Int. J. Cancer (2007) 121:2307-16, and Ohri et al, Cancer Biol. Ther. (2007) Apr. 20; 6(7) (Epub ahead of print)). Of 21 siRNAs screened, OCM-8054 (SEQ ID NO: 59) was the most effective in inhibiting expression of BORIS protein as assessed by densitometry analysis of Western blots following siRNA treatment.

Figure 2:
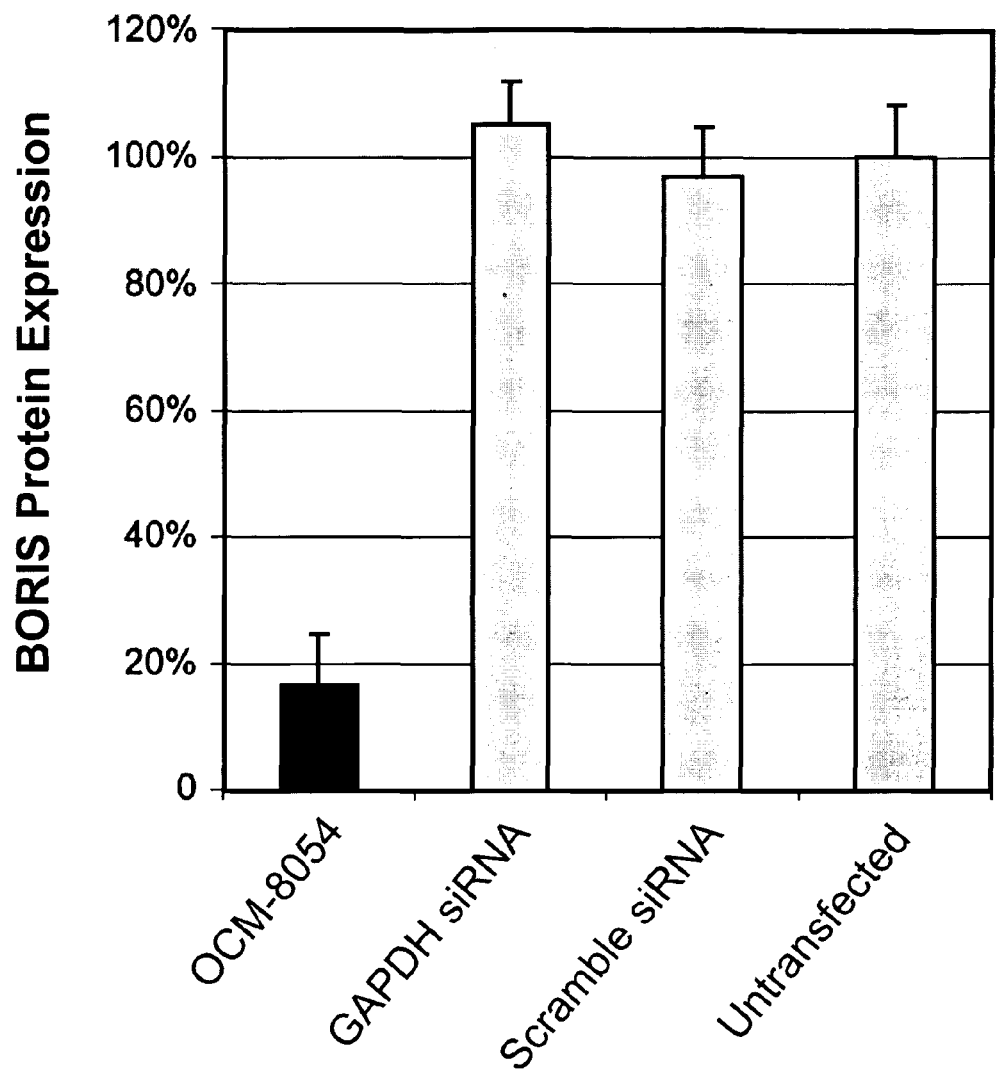
FIG. 2. illustrates that OCM-8054 (SEQ ID NO:59) siRNA dramatically inhibits expression of BORIS in MDA-MB-231 breast cancer cells.

Endogenous expression of BORIS was detected in untreated MDA-MB-231 by Western blotting, but not in control epithelial cells. Transfection (50 nM) of MDA-MB-231 cells with BORIS siRNA (OCM-8054; SEQ ID NO: 59), but not GAPDH siRNA or scrambled siRNA, reduced BORIS expression. Importantly, the OCM-8054 (SEQ ID NO: 59) siRNA-mediated inhibition of BORIS was specific since no inhibition was observed with scrambled siRNA sequences or with control siRNA directed to unrelated GAPDH sequences. The density and thickness of bands on the Western blots were calculated and plotted (FIG. 2). MDA-MB-231 cells transfected with OCM-8054 (SEQ ID NO: 59) (black) showed reduced BORIS expression, while cells transfected with GAPDH or scrambled siRNA resulted in BORIS expression levels similar to untransfected controls.

Example 3

Selective Reduction of Breast Cancer Cell Viability by BORIS siRNA

The dependency of MDA-MB-231 breast cancer cell viability on BORIS expression was examined by silencing BORIS with OCM-8054 (SEQ ID NO: 59) siRNA. Cellular viability of MDA-MB-231 breast cancer and control cells transfected with BORIS siRNA (OCM-8054; SEQ ID NO: 59) was measured using the CellTiter 96® AQueous One Solution Cell Proliferation Assay (Promega, Madison, Wis.) at either 24- or 48-h post-transfection. The dose-dependent reduction in viability of BORIS siRNA transfected breast cancer cells was normalized to the respective viability of 50 nM scrambled or untransfected breast cancer cells. Hydrogen peroxide (20 μM) was used as a positive control for reduced cellular viability.

At the 24-h time point there was no significant reduction of viability in MDA-MB-231 or control cell lines. Only the positive control, hydrogen peroxide, induced a 66% decrease in cell viability at this time point (data not shown). However, at 48 h, a significant concentration-dependent decrease in viability was observed with MDA-MB-231 cancer cells (FIG. 3A), but not with control ARPE-19 cells (FIG. 3B) or HMEC control cells (not shown). Breast cancer cells transfected with 50 nM, 25 nM, 5 nM, and 1.7 nM OCM-8054 (SEQ ID NO: 59) siRNA showed 86%, 61%, 43%, and 15% reduction in viability, respectively. Neither control scrambled siRNA-transfected nor untransfected cells, demonstrated any change in viability over the two day time course. Of note, the viability of neither non-malignant control cell lines that do not express BORIS (ARPE-19 and HMEC) was affected by transfection with any concentration of OCM-8054 (SEQ ID NO: 59) siRNA tested (FIG. 3B and data not shown). This result excluded an interpretation of non-specific cellular killing by interfering with ubiq-uitous cellular processes. These data demonstrated that expression of BORIS is required for viability of the breast cancer cells, but not non-malignant cells.

Example 4

Inhibition of BORIS Expression by OCM-8054 siRNA Induces Apoptotic Death of MDA-MB-231 Breast Cancer via Caspase 3/7 Activation While not wishing to be bound to a particular theory, it has been speculated that many tumors, during their evolution, become reliant on the oncogenes that drive transformation, not simply for uncontrolled neoplastic growth, but to the point of cell death via active apoptosis in the absence of the oncogene. It was, therefore of interest to examine the mechanism involved in cell death associated with BORIS silencing.

However, the MTS determination of MDA-MB-231 cell death after BORIS silencing did not indicate whether the death was of a passive (necrosis) or active (apoptosis) form. Caspase 3/7 activation in cells transfected as described above in Example 3, was measured using the Caspase-Glo 3/7 Assay (Promega, Madison, Wis.) as recommended by the manufacturer at the either 24-or 48-h post-transfection. The dose-dependent increases in Caspase 3/7 activation of BORIS siRNA transfected breast cancer cells was normalized to the respective viability of 50 nM scrambled or untransfected breast cancer cells at the 24 (gray) and 48 (black) time points. Hydrogen peroxide (20 µM) was used a positive control for caspase activation and apoptosis. The results are shown in FIG. 4.

Figure 3:
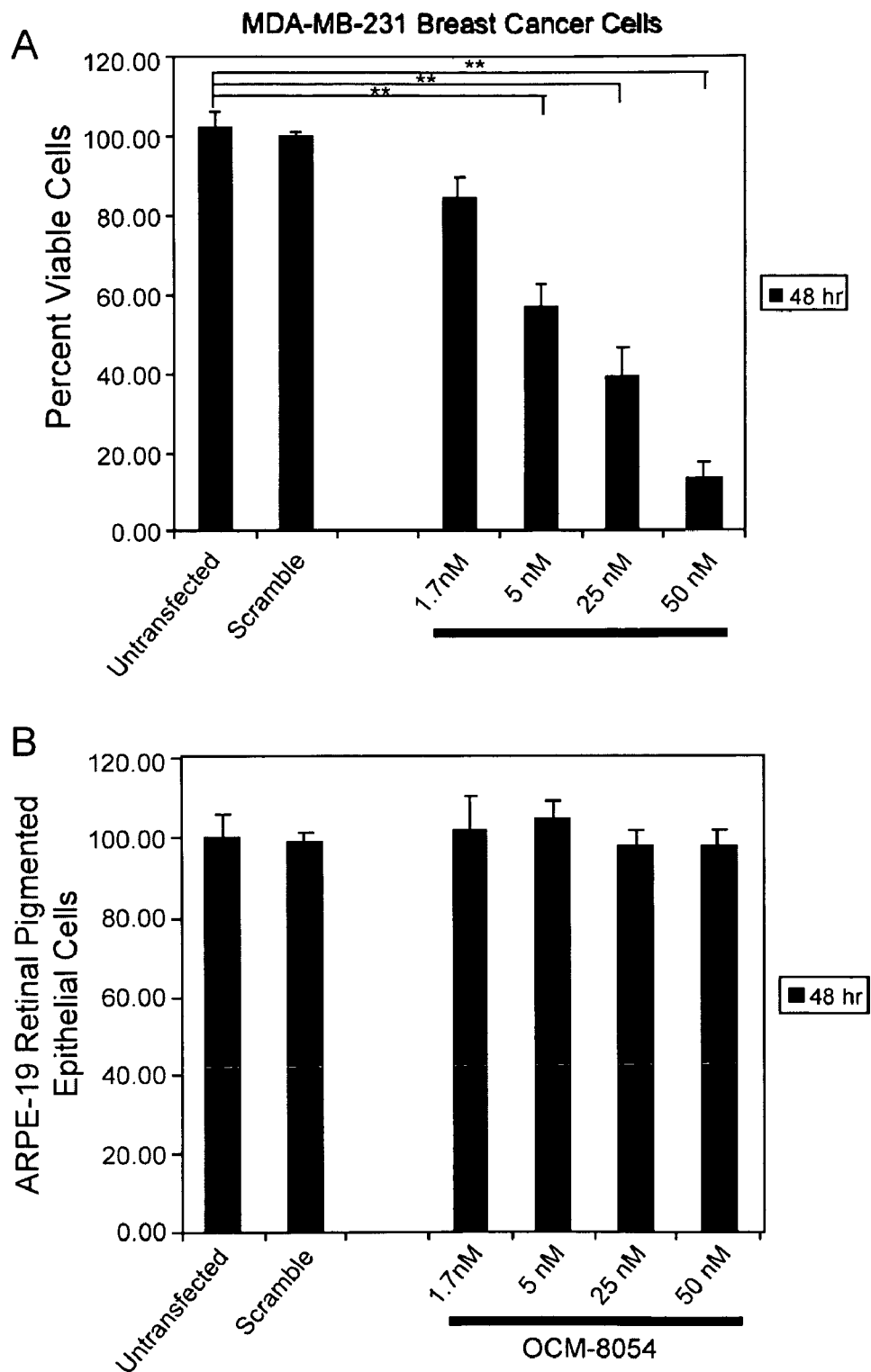
FIG. 3A is a histogram showing the dose-dependent effect of reducing MDA-MB-231 breast cancer cell viability by inhibiting BORIS gene expression with OCM-8054 (SEQ ID NO:59) siRNA, in comparison with control siRNA treatment.
FIG. 3B shows the effects of treating control epithelial cells with the same siRNAs as in FIG. 3A. The histograms are presented as means±SD. **P<0.01.
Figure 4:
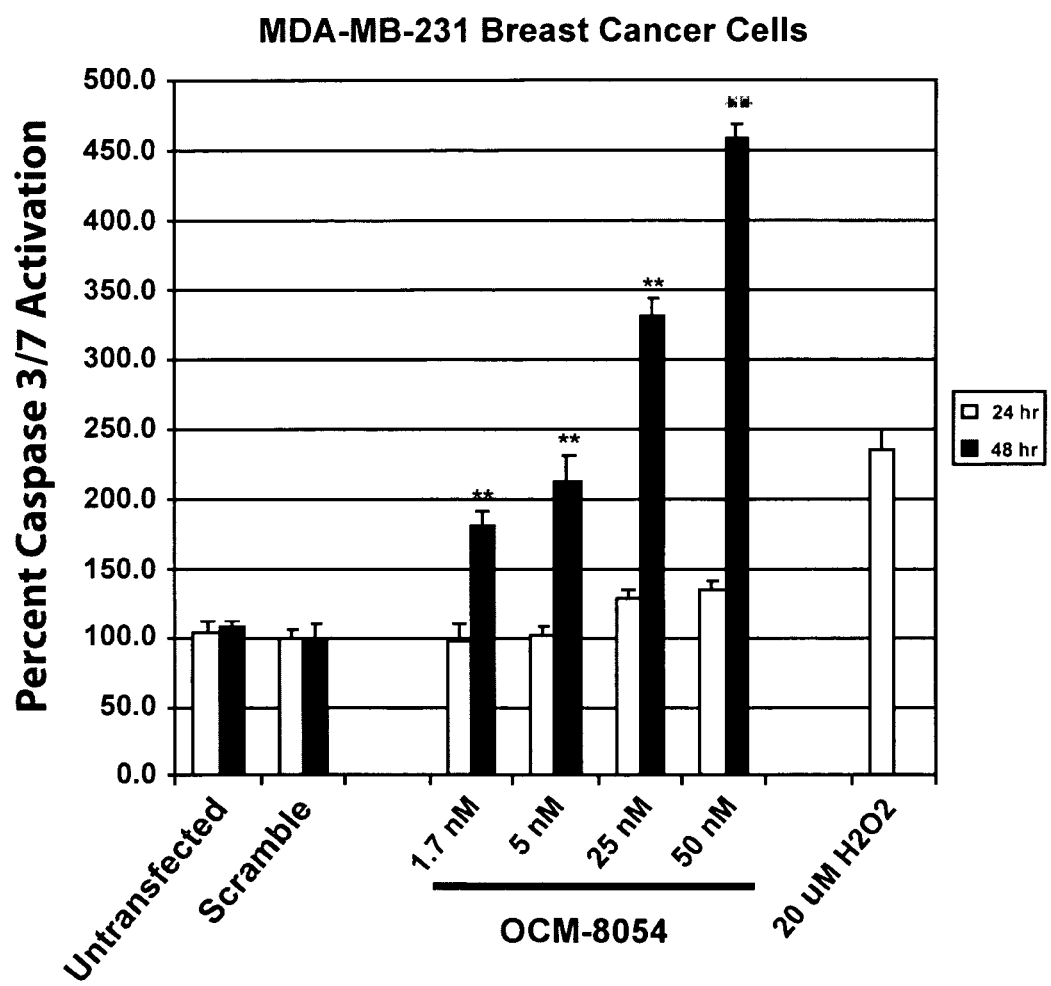
FIG. 4 shows the effects of inhibiting BORIS expression with OCM-8054 (SEQ ID NO:59) siRNA on Caspase 3/7 (an indicator of apoptotic death) in MDA-MB-231 breast cancer cells at 24 and 48 hours post-transfection. The histogram is presented as means±SD. **P<0.01.

At the 24-h post-transfection time point there were only small changes in caspase activity in tumor cells (FIG. 4). At 48 h, transfection with 50 nm, 25 nm, 5 nm, and 1.7 nm OCM-8054 (SEQ ID NO: 59) siRNA resulted in 458%, 330%, 212%, and a 180% increase in caspase activity, respectively. Neither control scrambled siRNA transfected nor untransfected cells demonstrated any gross change in caspase 3/7 activity over the two day time course. Importantly, the increased caspase activity was correlated with loss of viability (FIG. 3). Thus, BORIS-specific siRNA, OCM-8054 (SEQ ID NO: 59), but not control scrambled siRNA treatments were capable of inducing caspase 3/7 activity in a dose-dependent manner (FIG. 4). These data demonstrate that BORIS plays an essential role in survival of BORIS positive cancer cells and absence of this molecule induces apoptosis.

Example 5 siRNA Silencing in Glioblastoma Multiforme

Figure 5:
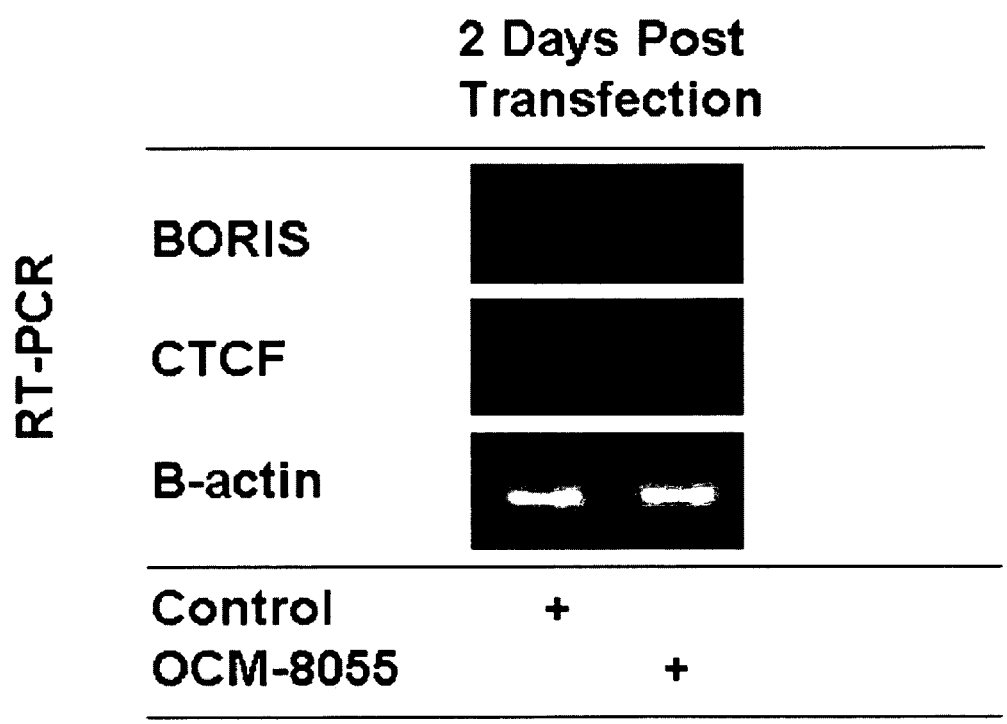
FIG. 5 shows BORIS, CTCF and B-actin mRNA expression 2 days after transfection with siRNA OCM-8055 (SEQ ID NO:60) as compared to controls.

Initially, the effect of siRNA silencing was tested on A-172 glioblastoma multiforme cells using OCM-8054 (SEQ ID NO:59), as described above. However, a similar amount of apoptotic cell death was not observed. Upon testing with other candidate BORIS siRNAs, OCM-8055 (SEQ ID NO:60) was found to reduce detectable BORIS mRNA (as detected by RT PCR; FIG. 5) as compared to controls. As shown in FIG. 5, OCM-8055 (SEQ ID NO:60) siRNA did not inhibit expression of CTCF or β-actin mRNA sequences.

Figure 6:
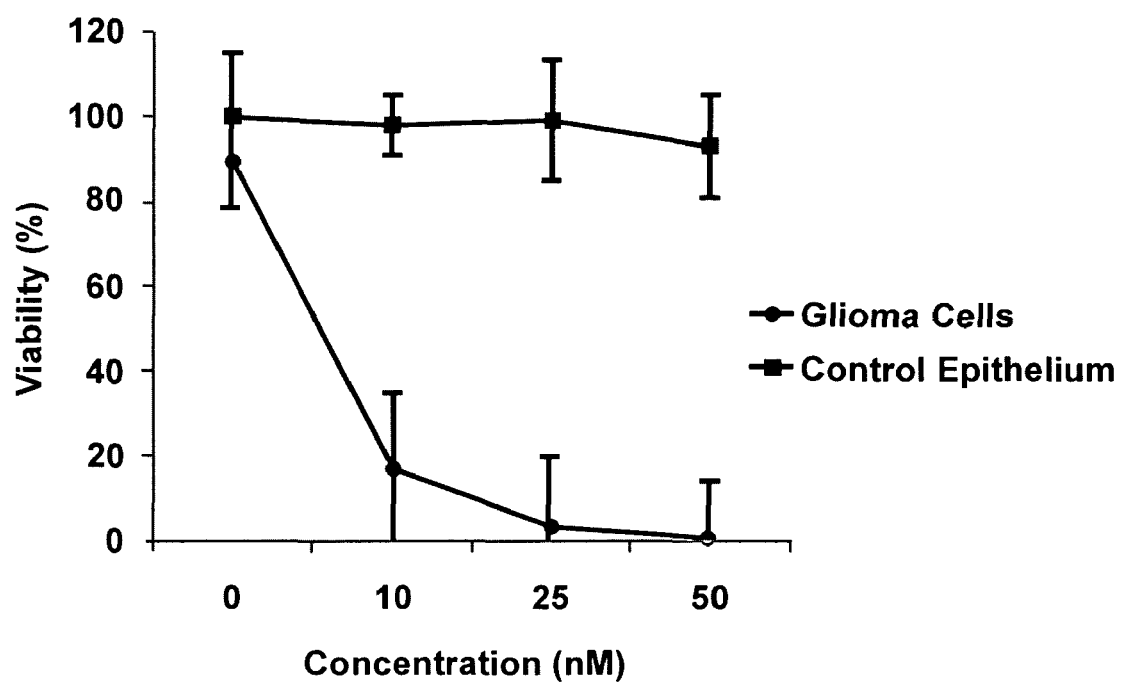
FIG. 6 shows the loss of viability following inhibition of BORIS expression with OCM-8055 (SEQ ID NO:60) siRNA in gilbastoma multiforme cells but not normal control epithelium.

Furthermore, significant apoptosis of glioblastoma cells was induced by OCM-8055 (SEQ ID NO:60) within a 72 hour time frame (FIG. 6). OCM-8055 (SEQ ID NO:60) activated apoptosis through a caspase dependent manner in glioblastoma cells but did not affect the viability or proliferation of non-malignant cells. OCM-8054 (SEQ ID NO:59) targets the mRNA region of BORIS that codes for zinc finger 10, while OCM-8055 (SEQ ID NO:60) targets the mRNA region of BORIS that codes for zinc finger 4.

Example 6

Identification of BORIS Variants for siRNA Targeting in Cancer

Published reports have focused on full-length BORIS molecules without regard to splice variants or truncations. GenBank lists 27 variants of BORIS, representing either DNA or amino acid sequence, that were deposited as direct submissions (i.e, were not reported in a published journal article), which are summarized below in Table 1.

TABLE 1

BORIS Variant Sequences

| BORIS VARIANT | GENBANK ACCESSION NO. | DATE POSTED | LENGTH (bp) |
| --- | --- | --- | --- |
| BORIS | NM_080618 | 15 Jun. 2008 | 3493 |
| A1 | DQ778108 | 1 Jul. 2007 | 3601 |
| A2 | DQ778109 | 1 Jul. 2007 | 3701 |
| A3 | DQ778112 | 1 Jul. 2007 | 3897 |
| A4 | DQ778113 | 1 Jul. 2007 | 1529 |
| A5 | DQ778122 | 1 Jul. 2007 | 2297 |
| A6 | DQ778123 | 1 Jul. 2007 | 2348 |
| B1 | DQ778111 | 1 Jul. 2007 | 2506 |
| B2 | DQ778124 | 1 Jul. 2007 | 1489 |
| B3 | DQ778125 | 1 Jul. 2007 | 1700 |
| B4 | DQ778126 | 1 Jul. 2007 | 1642 |
| B5 | DQ778127 | 1 Jul. 2007 | 1515 |
| B6 | DQ778128 | 1 Jul. 2007 | 3708 |
| B7 | DQ778129 | 1 Jul. 2007 | 2895 |
| C1 | DQ778110 | 1 Jul. 2007 | 4073 |
| C2 | DQ778114 | 1 Jul. 2007 | 2001 |
| C3 | DQ778115 | 1 Jul. 2007 | 2826 |
| C4 | DQ778116 | 1 Jul. 2007 | 2431 |
| C5 | DQ778117 | 1 Jul. 2007 | 1827 |
| C6 | DQ778121 | 1 Jul. 2007 | 2336 |
| C7 | DQ778119 | 1 Jul. 2007 | 5045 |
| C8 | DQ778118 | 1 Jul. 2007 | 3463 |
| C9 | DQ778120 | 1 Jul. 2007 | 4322 |
| F6 | DQ778130 | 1 Jul. 2007 | 745 |
| F7 | DQ778131 | 1 Jul. 2007 | 605 |
| BORIS | DQ294738 | 1 Dec. 2006 | 3822 |
| BORIS | AF336042 | 16 May 2002 | 3500 |

Figure 7:
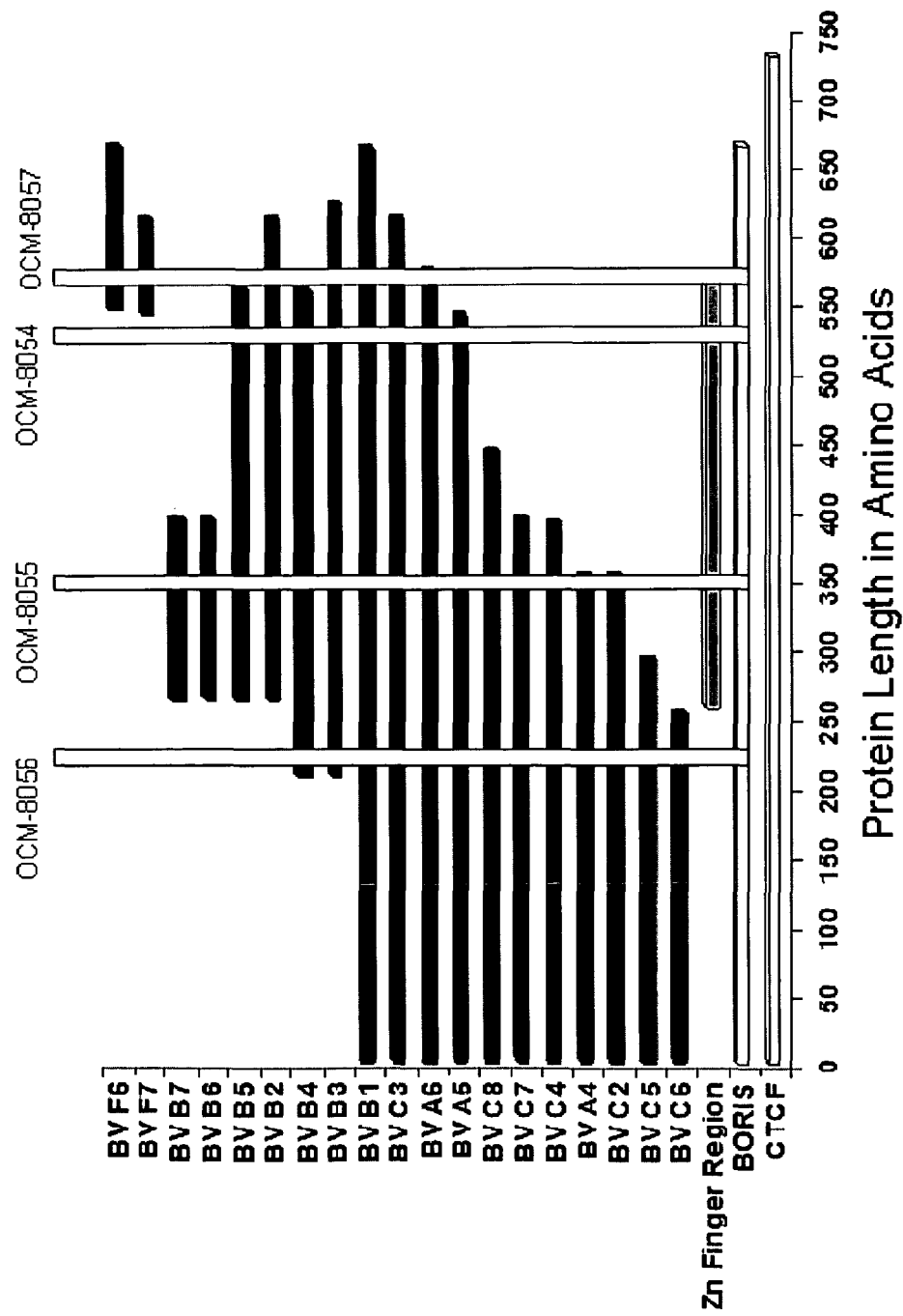
FIG. 7 shows an alignment of known variants of BORIS and the relative positions of the zinc finger region of the protein. This figure also shows the relative targeting location of siRNAs OCM-8054 (SEQ ID NO:59), OCM-8055 (SEQ ID NO:60), OCM-8056 (SEQ ID NO:61), and OCM-8057 (SEQ ID NO:13).

The variants represent both N-terminal and C-terminal deletions of BORIS, including deletions of part or all of the 11 zinc finger DNA binding domain. Computer analysis of the DNA and amino acid sequences of the known BORIS variants (BV) using Geneious 3.7.1 software yielded an initial alignment of the amino acid sequences of the conserved regions for all BORIS variants as shown in FIG. 7. The diversity of BORIS variants, designated BV-A1 to BV-F7 (black bars), is apparent when compared to the full length BORIS protein sequence (top white bar). The position of CTCF (bottom white bar) is shown for comparison even though its sequence is divergent. The position of the 11 zinc finger domain in BORIS (grey bar) illustrates that many reported BORIS variants lack some or all of the zinc fingers that are necessary for its DNA interaction in the function of BORIS as a transcription factor.

This figure also shows the approximate position of the siRNA target regions for OCM-8054 (SEQ ID NO:59), OCM-8055 (SEQ ID NO:60), OCM-8056 (SEQ ID NO:61) and OCM-8057 (SEQ ID NO:13) (vertical bars). From this figure, it is clear that individual siRNAs may be ineffective for certain BORIS variants. Thus it is important to determine which variant BORIS protein is expressed in a particular cancer type in order to target the appropriate siRNA to the cancer.

Example 7

Identification and Targeting of BORIS and BORIS Variants in Primary Tumors

Primary tumor biopsies samples are obtained from human patients. The pathology of the biopsy sample is confirmed using standard histopathological techniques. Total RNA is extracted from the sample using RNeasy sample preparation (Qiagen, Carlsbad, Calif.). cDNA is synthesized from 2 µg of total RNA with oligo(dT)20 primers using the Superscript III reverse transcriptase system (Invitrogen, Carlsbad, Calif.) per the manufacturer's protocol. Quantitative RT-PCR is performed with the Light Cycler real-time PCR system (Roche, Germany) using primers that flank various siRNA target regions for inhibition of BORIS expression. Primer sequences may include: GAPDH, 5'-GTT GTC TCC TGC GAC TTC A-3' (forward; SEQ ID NO:124)) and 5'-GGT GGT CCA GGG TTT CTT A-3' (reverse; SEQ ID NO:125); human (h)BORIS, 5'-AAG ACC ATC GGA GCC CTA GT-3' (nt128-148, forward; SEQ ID NO:126) and 5'-ATC CTG CAA CTC CAC AGC TT-3' (nt300-280, reverse; SEQ ID NO:127). The individual PCR reactions consist of a hot-start Taq Polymerase activation step of 94° C. for 3 minutes, followed by conditions shown to produce unique, specific bands for each mRNA (e.g. 35 cycles only). Expression levels of mRNA for each gene are calculated using standard curves produced with the relevant cloned BORIS cDNA (pVAX-hBORIS) and corrected for control genes (GAPDH and β-actin). All amplicons cross introns to avoid amplification of genomic DNA. The identity of PCR products is confirmed by agarose gel electrophoresis and DNA sequence analysis. Virtually all biopsy samples that are confirmed as neoplastic tissue demonstrate expression of BORIS or a BORIS variant. More aggressive tumors have higher levels of BORIS expression.

siRNA is synthesized by and purchased from Qiagen-Xeragon or Ambion. The sequence of siRNA targeted against BORIS is selected from Sequence ID NOs:1-123, based on the presence of the target region for each in mRNA from the cancer biopsy sample. siRNA is resolved in a suspension buffer (100 nM potassium acetate, 30 mM HepesKOH, 2 nM Mg-acetate, pH 7.4), heated at 90° C. for 1 min and incubated for 1 h at 37° C. Then the solution is diluted 1:10 in a 10% lipid solution (Lipovenos) purchased from Fresenius Kabi (Bad Homburg, Germany) containing 100 g soya bean oil, 25 g glycerol and 6 g phospholipids from egg per litre. The solution is incubated for 15 min at room temperature and mixed multiple times by passing it through a small lumen syringe generating negative pressure using a three-way valve to form the lipid dispersion solution and reconstitute siRNA chylomicrons in the lipid solution.

siRNA injection (50 µg/kg siRNA) solution is administered intravenously as a bolus injection over 1-15 minutes before siRNA is administered to patients. Written informed consent is obtained. All aspects of clinical siRNA administration are approved by the local Institutional Review Board.

10 patients with BORIS-positive cancer are treated with BORIS-specific siRNA, whereas controls (n=10) are treated with mismatched siRNA.

Radiological examination reveals objective tumor response in 100% of patients treated with BORIS-specific siRNA. No responses are observed in patients receiving control mismatched siRNA.

---

What is claimed is:

1. A method of inhibiting expression of Brother of the Regulator of Imprinted Sites (BORIS) in a cell comprising introducing into the cell a small interfering RNA (siRNA) molecule that directs cleavage of BORIS mRNA, thereby inhibiting expression of BORIS in the cell, wherein the siRNA molecule is a double-strand RNA, RNA-DNA chimera or RNA-DNA hybrid, and wherein one strand of the siRNA has the nucleotide sequence of SEQ ID NOs:59.

2. A method of inhibiting expression of Brother of the Regulator of Imprinted Sites (BORIS) in a cell comprising introducing into the cell a small interfering RNA (siRNA) molecule that directs cleavage of BORIS mRNA, thereby inhibiting expression of BORIS in the cell, wherein the siRNA molecule is a double-strand RNA, RNA-DNA chimera or RNA-DNA hybrid, and wherein one strand of the siRNA has the nucleotide sequence of SEQ ID NOs:60.

3. The method of claim 2, wherein the small interfering RNA (siRNA) molecule does not inhibit expression of CTCF mRNA sequences in the cell.

4. The method of claim 2, wherein the siRNA is about 19-24 base pairs in length.

5. The method of claim 2, wherein the siRNA is about 21-22 base pairs in length.

6. The method of claim 2, wherein the siRNA is a duplex consisting of a sense strand and an antisense strand, wherein:
   a) each strand is 19-24 nucleotides in length;
   b) the duplex has 19-24 base pairs;
   c) the antisense strand is complementary to a target RNA encoded by the BORIS gene; and
   d) the sense strand and the antisense strand are complementary to each other.

7. The method of claim 2, wherein inhibiting expression of BORIS in the cell induces apoptosis of the cell.

8. The method of claim 2, wherein inhibiting expression of BORIS in the cell activates at least one DEVD-recognizing caspase in the cell.

9. The method of claim 2, wherein the cell is a mammalian cell.

10. The method of claim 9, wherein the mammal is a human cell.

11. The method of claim 2, wherein the cell is a cancer cell.

12. The method of claim 11, wherein the cancer cell is a breast, lung, skin, bone, brain, colon, prostate, pancreas, mast cell, ovarian or uterine cancer cell.

13. An siRNA molecule that directs cleavage of a BORIS mRNA comprising the polynucleotide sequence of SEQ ID NO:60.

14. A method of inhibiting expression of a BORIS variant in a cell comprising
   a) detecting expression of a BORIS variant in the cell; and
   b) introducing into the cell a small interfering siRNA molecule that directs cleavage of an mRNA encoding the variant BORIS, thereby inhibiting expression of the variant BORIS in the cell, wherein the siRNA molecule is a double-strand RNA, RNA-DNA chimera or RNA-DNA hybrid, and wherein one strand of the siRNA has the nucleotide sequence of SEQ ID NO:59.

15. The method of claim 14, wherein the variant is a splice variant, truncation or deletion variant.

16. The method of claim 14, wherein detecting expression of a variant BORIS in the cell, comprises PCR of RNA from the cell.

17. A method of inhibiting expression of a BORIS variant in a cell comprising
   a) detecting expression of a BORIS variant in the cell; and
   b) introducing into the cell a small interfering siRNA molecule that directs cleavage of an mRNA encoding the variant BORIS, thereby inhibiting expression of the variant BORIS in the cell, wherein the siRNA molecule is a double-strand RNA, RNA-DNA chimera or RNA-DNA hybrid, and wherein one strand of the siRNA has the nucleotide sequence of SEQ ID NO:60.

18. The method of claim 17, wherein the variant is a splice variant, truncation or deletion variant.

19. The method of claim 17, wherein detecting expression of a variant BORIS in the cell, comprises PCR of RNA from the cell.

* * * * *

SEQUENCE LISTING

```
<160> NUMBER OF SEQ ID NOS: 129

<210> SEQ ID NO 1
<211> LENGTH: 22
<212> TYPE: RNA
<213> ORGANISM: Artificial Sequence
<220> FEATURE:
<223> OTHER INFORMATION: synthetic oligonucleotide

<400> SEQUENCE: 1
vaaagaacuc gaguugaugc cg                                          22

<210> SEQ ID NO 2
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 2
aagaacucga guugaugccg g                                           21

<210> SEQ ID NO 3
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 3
aaaaaggccu gaaggaggag g                                           21
```

```
<210> SEQ ID NO 4
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 4
aaaaggccug aaggaggagg a                                                    21

<210> SEQ ID NO 5
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 5
aaaaagacgg agugugcaga g                                                    21

<210> SEQ ID NO 6
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 6
aaaagacgga gugugcagag a                                                    21

<210> SEQ ID NO 7
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 7
aaagacggag ugugcagaga g                                                    21

<210> SEQ ID NO 8
<211> LENGTH: 21
<212> TYPE: RNA
<213> ORGANISM: Artificial Sequence
<220> FEATURE:
<223> OTHER INFORMATION: synthetic oligonucleotide

<400> SEQUENCE: 8
aagacggagu gugcagagag a                                                    21

<210> SEQ ID NO 9
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 9
aagcugugga guugcaggau a                                                    21

<210> SEQ ID NO 10
<211> LENGTH: 21
<212> TYPE: RNA
<213> ORGANISM: Artificial Sequence
<220> FEATURE:
<223> OTHER INFORMATION: synthetic polynucleotide
```

```
<400> SEQUENCE: 10
aaacgcucac uucaggaaau a                                              21

<210> SEQ ID NO 11
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 11
aacgcucacu ucaggaaaua c                                              21

<210> SEQ ID NO 12
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 12
aaaugcucca aguguggcaa a                                              21

<210> SEQ ID NO 13
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 13
aaccugcaca gacauucgga g                                              21

<210> SEQ ID NO 14
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 14
aacaagaaag aggaagcaga c                                              21

<210> SEQ ID NO 15
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 15
aaaaagacgg agugugcaga g                                              21

<210> SEQ ID NO 16
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 16
aagaaagagg aagcagacca u                                              21

<210> SEQ ID NO 17
<211> LENGTH: 21
```

-continued

```
<212> TYPE: RNA
<213> ORGANISM: Artificial Sequence
<220> FEATURE:
<223> OTHER INFORMATION: synthetic polynucleotide

<400> SEQUENCE: 17
aaagaggaag cagaccaucc u                                              21

<210> SEQ ID NO 18
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 18
aagaggaagc agaccauccu g                                              21

<210> SEQ ID NO 19
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 19
aaaccacagc cagagucaaa g                                              21

<210> SEQ ID NO 20
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 20
aaagaggaag uggaugaagg c                                              21

<210> SEQ ID NO 21
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 21
aaaagacgga gugugcagag a                                              21

<210> SEQ ID NO 22
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 22
aacacgaugg auaagugaga g                                              21

<210> SEQ ID NO 23
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 23
aagugagaga gagucagguu g                                              21
```

<210> SEQ ID NO 24
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 24
aaauagucua gaccagcuag u                                              21

<210> SEQ ID NO 25
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 25
aauagucuag accagcuagu g                                              21

<210> SEQ ID NO 26
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 26
aauuaugcuc cuuggcaggu a                                              21

<210> SEQ ID NO 27
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 27
aaggcaaaug uguaccugua a                                              21

<210> SEQ ID NO 28
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 28
aagcucgagg aagagcagga g                                              21

<210> SEQ ID NO 29
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 29
aagaaccagu uauuggcuga a                                              21

<210> SEQ ID NO 30
<211> LENGTH: 21
<212> TYPE: RNA
<213> ORGANISM: Artificial Sequence
<220> FEATURE:
<223> OTHER INFORMATION: synthetic polynucleotide

```
<400> SEQUENCE: 30
aaccaguuau uggcugaaag a                                              21

<210> SEQ ID NO 31
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 31
aaagaacaaa ggagcagcuc u                                              21

<210> SEQ ID NO 32
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 32
aaagacggag ugugcagaga g                                              21

<210> SEQ ID NO 33
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 33
aaugucagga gaugaaagaa g                                              21

<210> SEQ ID NO 34
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 34
aagugacgaa auuguucuca c                                              21

<210> SEQ ID NO 35
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 35
aaauguggaa gaacaagagg a                                              21

<210> SEQ ID NO 36
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 36
aauguggaag aacaagagga u                                              21

<210> SEQ ID NO 37
<211> LENGTH: 21
```

-continued

```
<212> TYPE: RNA
<213> ORGANISM: Artificial Sequence
<220> FEATURE:
<223> OTHER INFORMATION: synthetic polynucleotide

<400> SEQUENCE: 37
aagaacaaga ggaucaaccu a                                              21

<210> SEQ ID NO 38
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 38
aaaccuuccg uacggucacu c                                              21

<210> SEQ ID NO 39
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 39
aaauguucca ugugcaagua u                                              21

<210> SEQ ID NO 40
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 40
aaguaugcca gugggaggc a                                               21

<210> SEQ ID NO 41
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 41
aauugaagcg ccauguccga u                                              21

<210> SEQ ID NO 42
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 42
aagacggagu gugcagagag a                                              21

<210> SEQ ID NO 43
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 43
aaacgccaca ugagaacgca c                                              21
```

<210> SEQ ID NO 44
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 44
aacgccacau gagaacgcac u                                              21

<210> SEQ ID NO 45
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 45
aacuugcaug cuuacagcgc u                                              21

<210> SEQ ID NO 46
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 46
aagcaggaac gucauaugac c                                              21

<210> SEQ ID NO 47
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 47
aaauguuucc gacagaagca a                                              21

<210> SEQ ID NO 48
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 48
aagcugugga guugcaggau a                                              21

<210> SEQ ID NO 49
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 49
aauguuuccg acagaagcaa c                                              21

<210> SEQ ID NO 50
<211> LENGTH: 21
<212> TYPE: RNA
<213> ORGANISM: Artificial Sequence
<220> FEATURE:
<223> OTHER INFORMATION: synthetic polynucleotide

```
<400> SEQUENCE: 50
aagcaacuuc uaaacgcuca c                                              21

<210> SEQ ID NO 51
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 51
aaugcuccaa guguggcaaa g                                              21

<210> SEQ ID NO 52
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 52
aagcaaaguc ggcugcuuca g                                              21

<210> SEQ ID NO 53
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 53
aaagucggcu gcuucaggaa a                                              21

<210> SEQ ID NO 54
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 54
aagaagaaca agaaagagga a                                              21

<210> SEQ ID NO 55
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 55
aagaacaaga aagaggaagc a                                              21

<210> SEQ ID NO 56
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 56
aagcagacca uccugaagga a                                              21

<210> SEQ ID NO 57
<211> LENGTH: 21
```

```
<212> TYPE: RNA
<213> ORGANISM: Artificial Sequence
<220> FEATURE:
<223> OTHER INFORMATION: synthetic polynucleotide

<400> SEQUENCE: 57
aaccacagcc agagucaaag a                                              21

<210> SEQ ID NO 58
<211> LENGTH: 21
<212> TYPE: RNA
<213> ORGANISM: Artificial Sequence
<220> FEATURE:
<223> OTHER INFORMATION: synthetic polynucleotide

<400> SEQUENCE: 58
aagaggaagu ggaugaaggc g                                              21

<210> SEQ ID NO 59
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 59
ggaaauacca cgaugcaaat t                                              21

<210> SEQ ID NO 60
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 60
ggcaaguaaa uugaagcgct t                                              21

<210> SEQ ID NO 61
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 61
ggaucaaccu acagcuggut t                                              21

<210> SEQ ID NO 62
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 62
uuugcaucgu gguauuucct g                                              21

<210> SEQ ID NO 63
<211> LENGTH: 21
<212> TYPE: DNA
<213> ORGANISM: Artificial Sequence
<220> FEATURE:
<223> OTHER INFORMATION: synthetic RNA/DNA polynucleotide; 19
``` ribonucleotides with two 3' deoxyribonucleotides (thymidine)

<400> SEQUENCE: 63
gcgcuucaau uuacuugcct c                                             21

<210> SEQ ID NO 64
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 64
accagcugua gguugaucct c                                             21

<210> SEQ ID NO 65
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 65
aaggaacctt ccactgtgat g                                             21

<210> SEQ ID NO 66
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 66
aggaaccttc cactgtgatg t                                             21

<210> SEQ ID NO 67
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 67
ggaaccttcc actgtgatgt c                                             21

<210> SEQ ID NO 68
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 68
accttccact gtgatgtctg c                                             21

<210> SEQ ID NO 69
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 69
ccttccactg tgatgtctgc a                                             21

```
<210> SEQ ID NO 70
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 70
ctgtgatgtc tgcatgttca c                                                  21

<210> SEQ ID NO 71
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 71
tgtctgcatg ttcacctctt c                                                  21

<210> SEQ ID NO 72
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 72
tgttcacctc ttctagaatg t                                                  21

<210> SEQ ID NO 73
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 73
cctcttctag aatgtcaagt t                                                  21

<210> SEQ ID NO 74
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 74
caaaggagca gcucuuuuut t                                                  21

<210> SEQ ID NO 75
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 75
aggagcagcu cuuuuugut t                                                   21

<210> SEQ ID NO 76
<211> LENGTH: 21
<212> TYPE: DNA
<213> ORGANISM: Artificial Sequence
<220> FEATURE:
<223> OTHER INFORMATION: synthetic RNA/DNA polynucleotide; 19
```

<210> SEQ ID NO 77
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 76
acaaugucag gagaugaaat t                                              21

<210> SEQ ID NO 77
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 77
ugucaggaga ugaaagaagt t                                              21

<210> SEQ ID NO 78
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 78
agaagugacg aaauuguuct t                                              21

<210> SEQ ID NO 79
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 79
gugacgaaau uguucucact t                                              21

<210> SEQ ID NO 80
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 80
auuguucuca caguuucaat t                                              21

<210> SEQ ID NO 81
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 81
auucaaaugu ggaagaacat t                                              21

<210> SEQ ID NO 82
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

-continued

```
<400> SEQUENCE: 82
auguggaaga acaagaggat t                                            21

<210> SEQ ID NO 83
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 83
aaugucccca aauaccagut t                                            21

<210> SEQ ID NO 84
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 84
aagcgaccua cgugugcaut t                                            21

<210> SEQ ID NO 85
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 85
cuugcaugcu uacagcgcut t                                            21

<210> SEQ ID NO 86
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 86
aacucauaag aaugagaagt t                                            21

<210> SEQ ID NO 87
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 87
gaaugagaag agguucaagt t                                            21

<210> SEQ ID NO 88
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 88
```

```
gugcaaacac ugcaguuaut t                                              21

<210> SEQ ID NO 89
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 89
gcaggaacgu cauaugacct t                                              21

<210> SEQ ID NO 90
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 90 auguuccga cagaagcaat t                                               21

<210> SEQ ID NO 91
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 91
acgcucacuu caggaaauat t                                              21

<210> SEQ ID NO 92
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 92
auaccacgau gcaaauuuct t                                              21

<210> SEQ ID NO 93
<211> LENGTH: 21
<212> TYPE: DNA
<213> ORGANISM: Artificial Sequence
<220> FEATURE:
<223> OTHER INFORMATION: synthetic RNA/DNA polynucleotide; 19
      ribonucleotides with two 3' deoxyribonucleotides (thymidine)

<400> SEQUENCE: 93
auuucauccc gacuguuuat t                                              21

<210> SEQ ID NO 94
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 94
uuucgucacu ucuuucauc                                                 19
```

```
<210> SEQ ID NO 95
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 95
ucucucucac uuauccauc                                               19

<210> SEQ ID NO 96
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 96
ucuuucuugu ucuucuucc                                               19

<210> SEQ ID NO 97
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 97
ugacucucuc ucacuuauc                                               19

<210> SEQ ID NO 98
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 98
uuguucuucu ucccuuucc                                               19

<210> SEQ ID NO 99
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 99 uuucggugc ugaaugagg                                                19

<210> SEQ ID NO 100
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 100
uuucaucucc ugacauugu                                               19

<210> SEQ ID NO 101
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 101
```

```
ucaugaguau guuuauagc                                                19

<210> SEQ ID NO 102
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 102
uucagcuugu agguaucuc                                                19

<210> SEQ ID NO 103
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 103
uuuagaaguu gcuucuguc                                                19

<210> SEQ ID NO 104
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 104
ucuagacacu accucaaac                                                19

<210> SEQ ID NO 105
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 105
uuugcaucgu gguauuucc                                                19

<210> SEQ ID NO 106
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 106
uauuugggga cauuucgc                                                 19

<210> SEQ ID NO 107
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 107
auuguuucaa agaaaaugc                                                19

<210> SEQ ID NO 108
<211> LENGTH: 19
<212> TYPE: RNA
<213> ORGANISM: Artificial Sequence
```

```
<220> FEATURE:
<223> OTHER INFORMATION: synthetic polynucleotide

<400> SEQUENCE: 108
auaugcacac guaggucgc                                                19

<210> SEQ ID NO 109
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 109
auucagucac aaugauggc                                                19

<210> SEQ ID NO 110
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 110
uaaaaacuuc uaacuugcu                                                19

<210> SEQ ID NO 111
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 111
aagacagcag aacaguagc                                                19

<210> SEQ ID NO 112
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 112
uuauugcaag aaaggcagg                                                19

<210> SEQ ID NO 113
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 113
uuaauccagc gggaaaagc                                                19

<210> SEQ ID NO 114
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 114
uugaggagca uuucacacc                                                19
```

<210> SEQ ID NO 115
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 115
uuaugaguuu ucuggugcu                                              19

<210> SEQ ID NO 116
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 116
uugaaccucu ucucauucu                                              19

<210> SEQ ID NO 117
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 117
auaugacguu ccugcuugc                                              19

<210> SEQ ID NO 118
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 118
aacaauucua gacacuacc                                              19

<210> SEQ ID NO 119
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 119
uucuucccuu uccugaagc                                              19

<210> SEQ ID NO 120
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 120
aaccugacuc ucucucacu                                              19

<210> SEQ ID NO 121
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 121
augaguaugu uuauagcgc                                                 19

<210> SEQ ID NO 122
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 122
auucuuauga guuuucugg                                                 19

<210> SEQ ID NO 123
<211> LENGTH: 19
<212> TYPE: RNA
<213> ORGANISM: Artificial Sequence
<220> FEATURE:
<223> OTHER INFORMATION: synthetic polynucleotide

<400> SEQUENCE: 123
uaacugcagu guuugcacu                                                 19

<210> SEQ ID NO 124
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 124
gttgtctcct gcgacttca                                                 19

<210> SEQ ID NO 125
<211> LENGTH: 19
<212> TYPE: DNA
<213> ORGANISM: Artificial Sequence
<220> FEATURE:
<223> OTHER INFORMATION: synthetic oligonucleotide primer

<400> SEQUENCE: 125
ggtggtccag ggtttctta                                                 19

<210> SEQ ID NO 126
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 126
aagaccatcg gagccctagt                                                20

<210> SEQ ID NO 127
<211> LENGTH: 20
<212> TYPE: DNA
<213> ORGANISM: Artificial Sequence
<220> FEATURE:
<223> OTHER INFORMATION: synthetic oligonucleotide primer

<400> SEQUENCE: 127
atcctgcaac tccacagctt                                                20

<210> SEQ ID NO 128
<211> LENGTH: 96
<212> TYPE: DNA
<213> ORGANISM: Homo sapiens

```
<400> SEQUENCE: 128
tgcctttctt gcaataaatg tttccgacag aagcaacttc taaacgctca cttcaggaaa         60
taccacgatg caaatttcat cccgactgtt tacaaa                                   96

<210> SEQ ID NO 129
<211> LENGTH: 96
<212> TYPE: DNA
<213> ORGANISM: Homo sapiens

<400> SEQUENCE: 129
tgcctggcct gcaacaagca cttccgacag aagcagctac tgaccgtgca cctgaggaag         60
taccatgacc cgaacttcgt ccccaatctg cacctg                                   96
```